(12) United States Patent
Desai et al.

(10) Patent No.: US 9,850,221 B2
(45) Date of Patent: Dec. 26, 2017

(54) SULFATED AND UNSULFATED FLAVONOID OLIGOMERS AS CANCER THERAPEUTICS

(71) Applicant: VIRGINIA COMMONWEALTH UNIVERSITY, Richmond, VA (US)

(72) Inventors: Umesh R. Desai, Glen Allen, VA (US); Rajesh Karuturi, Richmond, VA (US); Bhaumik B. Patel, Glen Allen, VA (US); Nirmita J. Patel, Glen Allen, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 15/034,232

(22) PCT Filed: Nov. 7, 2014

(86) PCT No.: PCT/US2014/064481
§ 371 (c)(1),
(2) Date: May 4, 2016

(87) PCT Pub. No.: WO2015/069979
PCT Pub. Date: May 14, 2015

(65) Prior Publication Data
US 2016/0280676 A1 Sep. 29, 2016

Related U.S. Application Data

(60) Provisional application No. 61/901,713, filed on Nov. 8, 2013.

(51) Int. Cl.
C07D 311/30 (2006.01)
C07D 405/12 (2006.01)
C07D 407/12 (2006.01)

(52) U.S. Cl.
CPC .......... *C07D 311/30* (2013.01); *C07D 405/12* (2013.01); *C07D 407/12* (2013.01)

(58) Field of Classification Search
None
See application file for complete search history.

(56) References Cited

U.S. PATENT DOCUMENTS

2009/0054516 A1    2/2009  Wu et al.
2015/0011513 A1*   1/2015  Chow .................. C07D 405/14
                                                  514/151

FOREIGN PATENT DOCUMENTS

EP         2119434 A1    11/2009

OTHER PUBLICATIONS

Liao et al., "Cyclohexylmethyl Flavonoids Suppress Propagation of Breast Cancer Stem Cells via Downregulation of NANOG", Evidence-Based Complementary and Alternative Medicine, Mar. 2, 2013, vol. 2013, p. 1-14.
Ren et al., "Flavonoids: Promising Anticancer Agents", Medicinal Research Reviews, 2003, vol. 23, No. 4, p. 519-534.

* cited by examiner

*Primary Examiner* — Alicia L Otton
(74) *Attorney, Agent, or Firm* — Whitham, Curtis & Cook, P.C.

(57) ABSTRACT

Sulfated and unsulfated flavonoid oligomers as inhibitors of cancer stem cells (CSCs) are provided. In particular, sulfated flavonoid dimers are shown to selectively inhibit CSCs growth and self-renewal both in vitro and in vivo.

10 Claims, 19 Drawing Sheets

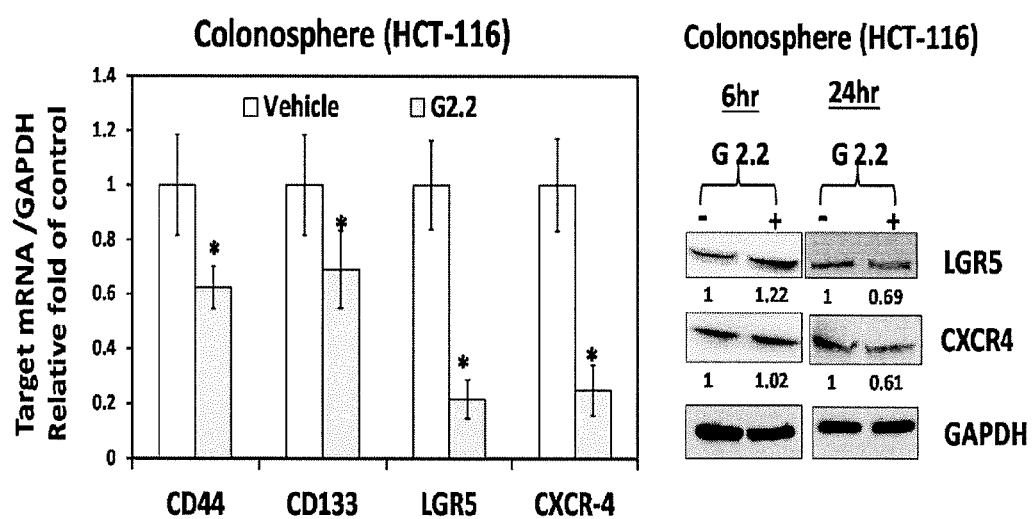
Figure 4A                    Figure 4B

US 9,850,221 B2

SULFATED AND UNSULFATED FLAVONOID OLIGOMERS AS CANCER THERAPEUTICS

BACKGROUND OF THE INVENTION

Field of the Invention

The invention generally relates to homogenous, synthetic, small molecules that selectively inhibit the growth of cancer stem cells, for example colorectal cancer stem cells, and prevent replacement or recurrence of the observed cancer.

Background of the Invention

The cancer stem-like cell (CSC) hypothesis has attracted a lot of attention as a unifying hypothesis that explains the shortcomings of current anti-cancer therapeutics and posits a paradigm-shifting direction for the discovery of potential, new anti-cancer agents (1,2). Primary and acquired resistances to cytotoxic therapies play a major role in disease recurrence in a majority of advanced epithelial malignancies including colorectal cancer. This phenomenon is thought to be the result of the extended survival of a small population of CSCs with the ability to self-renew and reconstitute the entire tumor (3). Additionally, the CSCs also possess the ability to invade and metastasize, which is more detrimental in a majority of cases. A new approach is critically needed to prevent disease recurrence arising from inability to destroy CSCs.

A therapeutic paradigm that is gaining momentum is targeting CSCs through either inhibition of CSC self-renewal or induction of differentiation, should be singularly effective in eradicating a tumor (4,5). Further, CSC targeting may display an added advantage of a 'magic bullet' because of the possibility of simultaneously treating several types of cancers arising from the mechanistic similarity expected at the CSC level.

Although attractive, targeting CSCs is intrinsically challenging. CSCs comprise only a small percent of the overall tumor cell population, which implies that high-throughput screening (HTS) approaches that utilize bulk cancer cells are likely to not identify CSC-specific agents. Gupta et al. have used epithelial-mesenchymal transition (EMT) in a breast cancer cell line to enhance the proportion of CSCs, which enabled application of HTS on a library of small molecules and extracts. The work resulted in the identification of salinomycin, but not paclitaxel (a known anticancer drug), as a preferential inhibitor of CSCs (6). Recent application of this technology has led to identification of three probes from the NIH Molecular Libraries Program as potent inhibitors of breast CSCs (7-11). While salinomycin is a polyketide synthase-derived natural product, probes ML239, ML243 and ML245 are chemically synthesizable, small hydrophobic molecules. The identification of only four molecules targeting CSC (and that to only breast CSC) in the past five years highlights the difficulty of identifying CSC-based therapeutics. For the CSC paradigm to translate into therapeutic success, a more fundamental and generalizable approach is needed.

SUMMARY OF THE INVENTION

The invention provides GAG mimetics that are the first molecules to selectively target cancer stem cells. The GAG mimetics are synthetic molecules (as opposed to naturally occurring). The GAG mimetics may be used in a variety of cancer therapies. These GAG mimetics are small molecules (not polymers) and fully homogenous, which offer several therapeutic advantages. The GAG mimetics target one or more fundamental pathways which are important to CSCs from other tissues including colorectal. Thus, strategies and therapeutic agents developed for colon cancer can be applied to other cancers as well.

BRIEF DESCRIPTION OF THE DRAWINGS

FIG. 4A-B. Effects of G2.2 on the mRNA levels of CSC markers at 6 h (A). Real-time quantitative reverse transcriptase polymerase chain reaction was used to determine relative mRNA expression of CSC genes and GAPDH served as house-keeping control. (B) shows the protein expression of select CSC markers LGR5 and CXCR4 at 6- and 24-hours following treatment with G2.2 (100 µM) or vehicle. Numbers under the blot in (B) show the relative change in expression levels of the marker in comparison to vehicle-treated CSCs using densitometry. Error bars represent ±1 SEM. * represents p<0.01 compared to respective controls.

DETAILED DESCRIPTION

Figure 1A:
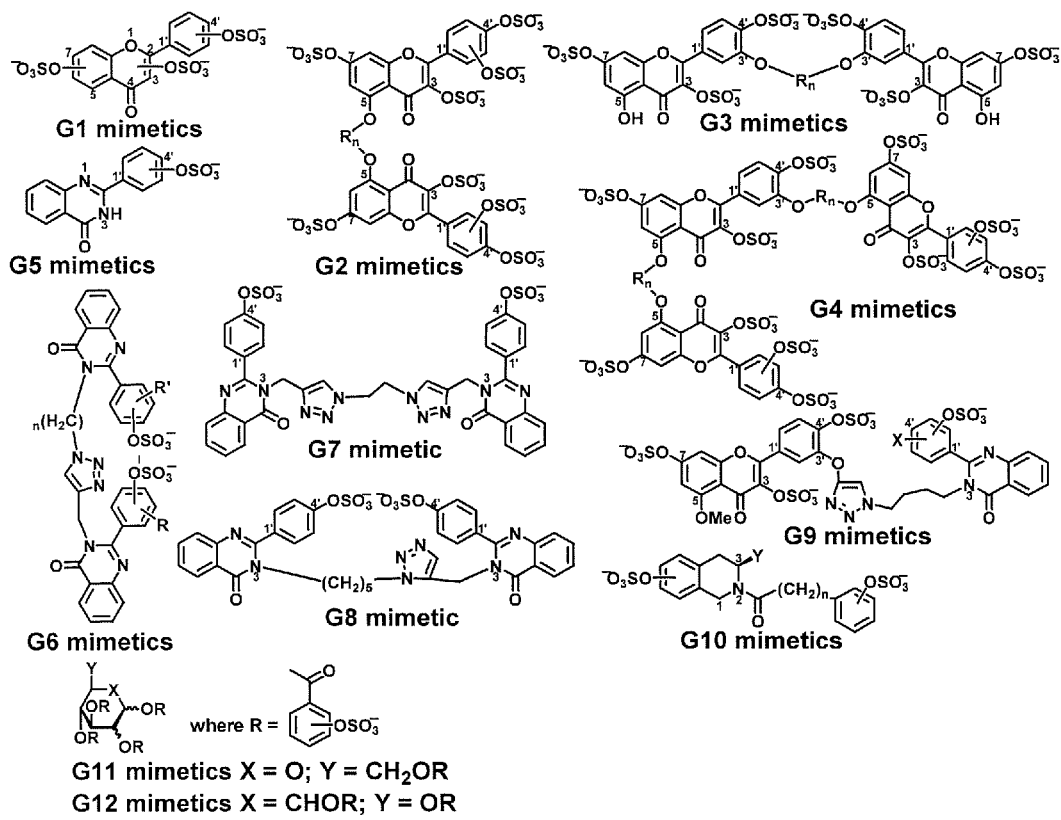
FIG. 1A-B. Selective targeting of colorectal cancer stem-like cells (CSCs) by tandem, dual screening of a focused sulfated NSGM library of 53 compounds belonging to 12 scaffolds. A. The scaffolds are labeled as G1 to G12 mimetics. 'R', 'n', 'X', and 'Y' represent structural variations. B. The protocol involved differential screening analysis of CSC growth under monolayer versus spheroid conditions (labeled 'Screen 1') followed by primary versus secondary/tertiary growth ('Screen 2'). The screen identified three 'lead' NSGMs, of which G2.2 was especially interesting because its two closely related analogs G1.4 and G4.1 were found to be inactive following screen 1 and screen 2, respectively. All 53 NSGMs were screened at 100 µM concentration.

Embodiments of the invention provide novel sulfated and unsulfated flavonoid oligomers as inhibitors of cancer stem cells. These molecules constitute new compositions of matter, and can be combined with other constituents and carriers (solid and liquid) to produce compositions having important clinical and research usage.

Embodiments of the invention provide sulfated flavonoid dimers having the general formula of formula I:

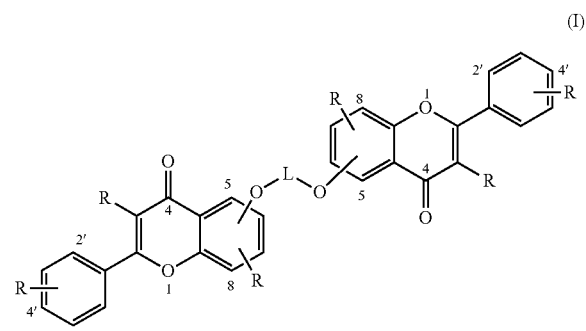

(I)

wherein

R is one or more of —OH, or —$OSO_3^-M^+$ or —H, each of which may be the same or different, and wherein at least one —$OSO_3^-M^+$ group is present in the molecule and wherein M is selected from the group consisting of $Na^+$, $K^+$, $Li^+$, $NH_4^+$, $NR'_4^+$, $Mg^{2+}$, $Ca^{2+}$ or other metal cations, wherein R' is H or alkyl or aryl groups;

L is any one of linkers $L_1$ through $L_9$ shown below wherein n is 1-10; and

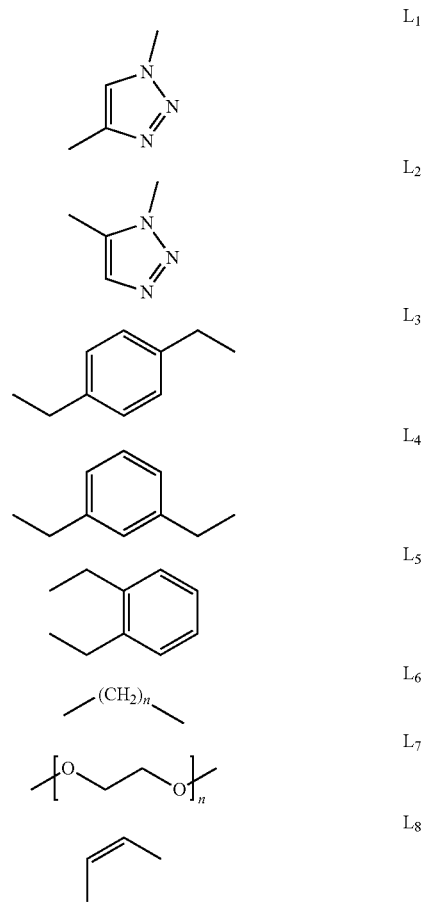

-continued

L$_9$
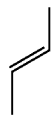

the two flavonoid units are connected through either 5-5, 5-6, 5-7, 5-8, 6-6, 6-7, 6-8, 7-7, 7-8, or 8-8 linkages.

Embodiments of the invention provide sulfated flavonoid dimers having the general formula of formula II:

(II)
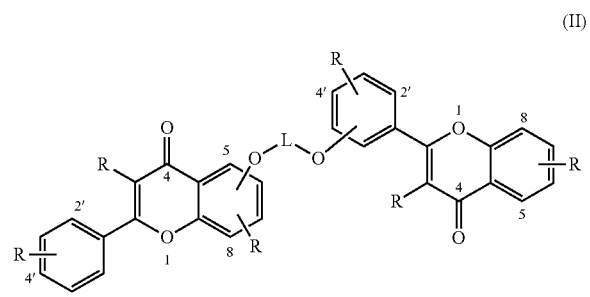

wherein

R is one or more of —OH, or —OSO$_3^-$M$^+$ or —H, each of which may be the same of different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$
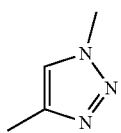

L$_2$
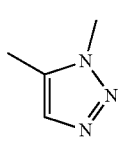

L$_3$
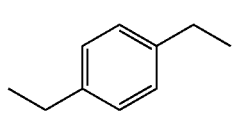

L$_4$
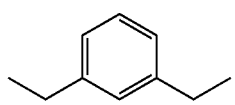

L$_5$
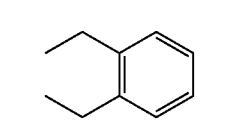

L$_6$
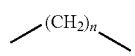

-continued

L$_7$
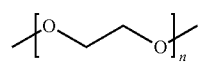

L$_8$

L$_9$
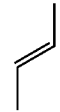

the two flavonoid units are connected through either 5-2', 5-3', 5-4', 6-2', 6-3', 6-4', 7-2', 7-3', 7-4', 8-2', 8-3', or 8-4' linkages.

Embodiments of the invention provide sulfated flavonoid dimers having the general formula of formula III:

(III)
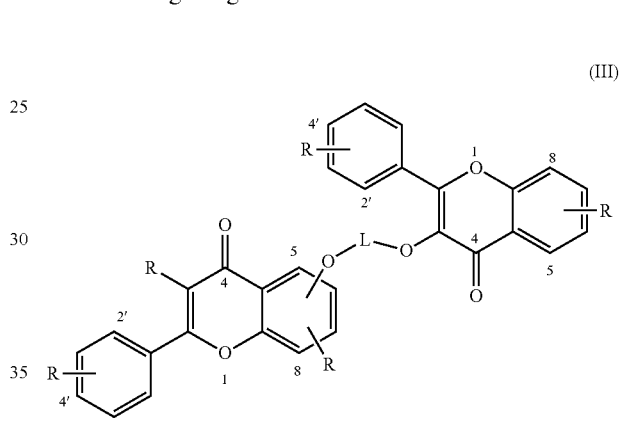

wherein

R is one or more of —OH, or —OSO$_3^-$M$^+$ or —H, each of which may be the same or different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$
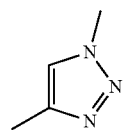

L$_2$
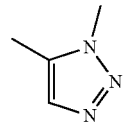

L$_3$
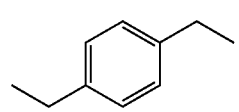

-continued

L$_4$

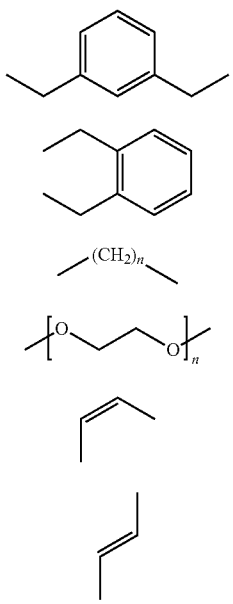

L$_5$

L$_6$

L$_7$

L$_8$

L$_9$ the two flavonoid units are connected through either 5-3, 6-3, 7-3, or 8-3 linkages.

Embodiments of the invention provide sulfated flavonoid dimers having the general formula of formula IV:

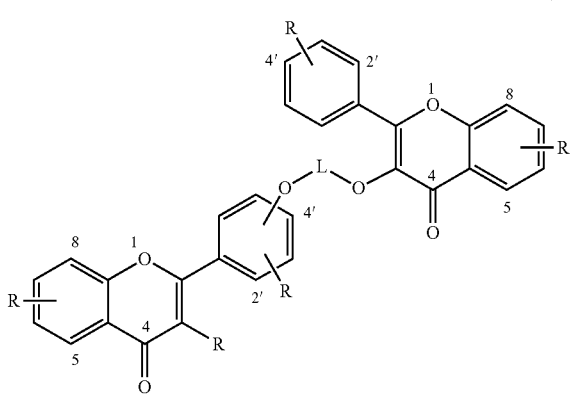

(IV)

wherein

R is one or more of —OH, or —OSO$_3^-$M$^+$ or —H, each of which may be the same or different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$

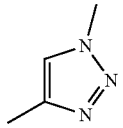

-continued

L$_2$

L$_3$

L$_4$

L$_5$

L$_6$

L$_7$

L$_8$

L$_9$

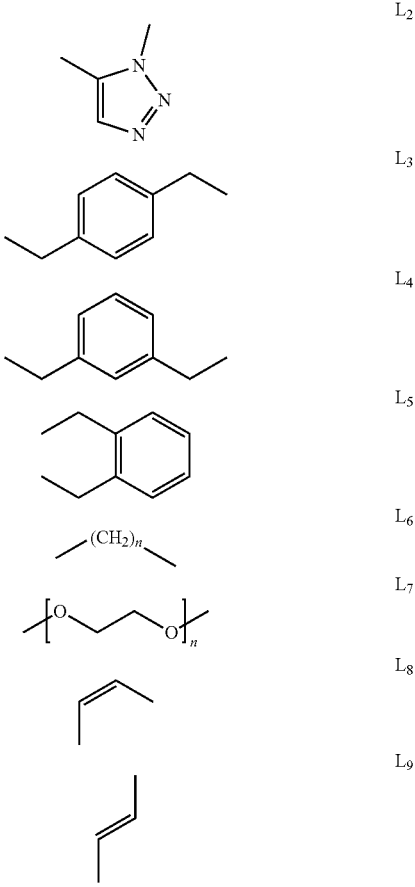

the two flavonoid units are connected through either 2'-3, 3'-3, or 4'-3 linkages.

Embodiments of the invention provide sulfated flavonoid dimers having the general formula of formula V:

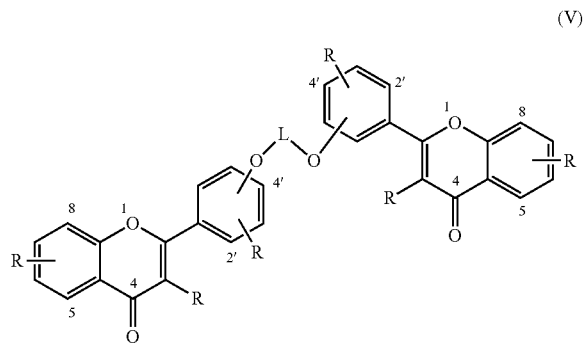

(V)

wherein

R is one or more of —OH, or —OSO$_3^-$M$^+$ or —H, each of which may be the same or different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L is any one of linkers $L_1$ through $L_9$ shown below wherein n is 1-10; and

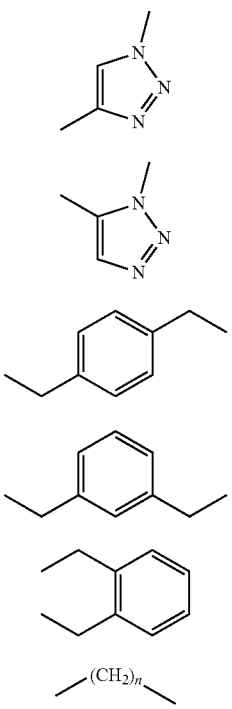

the two flavonoid units are connected through either 2'-2', 2'-3', 2'-4', 3'-3', 3'-4', or 4'-4' linkages.

Embodiments of the invention provide sulfated flavonoid dimers having the general formula of formula VI:

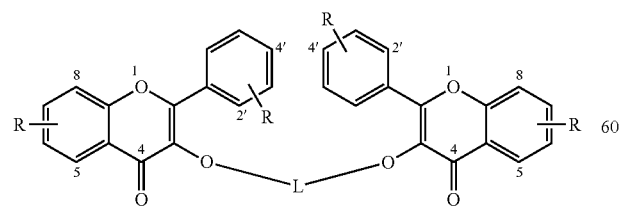

(VI)

wherein

R is one or more of —OH, or —$OSO_3^-M^+$ or —H, each of which may be the same or different, wherein at least one —$OSO_3^-M^+$ group is present in the molecule and wherein M is selected from the group consisting of $Na^+$, $K^+$, $Li^+$, $NH_4^+$, $NR'_4^+$, $Mg^{2+}$, $Ca^{2+}$ or other metal cations, wherein R' is H or alkyl or aryl groups;

L is any one of linkers $L_1$ through $L_9$ shown below wherein n is 1-10; and

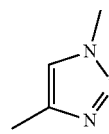
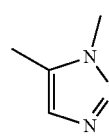
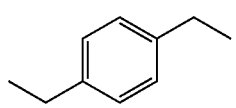
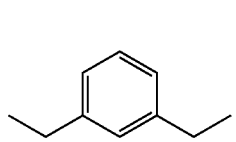
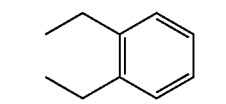
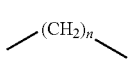
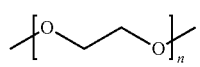
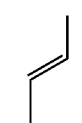

any two flavonoid units are connected through 3-3 linkage.

Embodiments of the invention provide sulfated flavonoid trimers having the general formula of formula VII:

(VII)

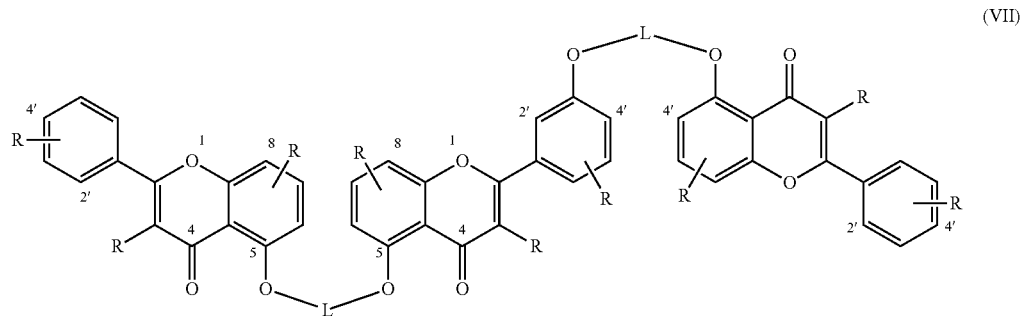

wherein
R is one or more of —OH, or —OSO$_3^-$M$^+$ or —H, each of which may be the same or different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

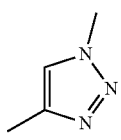
L$_1$

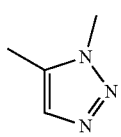
L$_2$

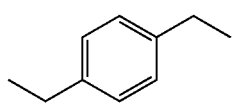
L$_3$

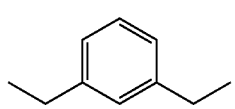
L$_4$

-continued

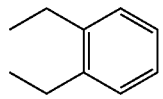
L$_5$

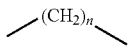
L$_6$

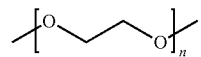
L$_7$

L$_8$

L$_9$ any two flavonoid units are connected through either 5-5, 5-6, 5-7, 5-8, 6-6, 6-7, 6-8, 7-7, 7-8, or 8-8 linkages.

Embodiments of the invention provide sulfated flavonoid tetramers having the general formula of formula VIII:

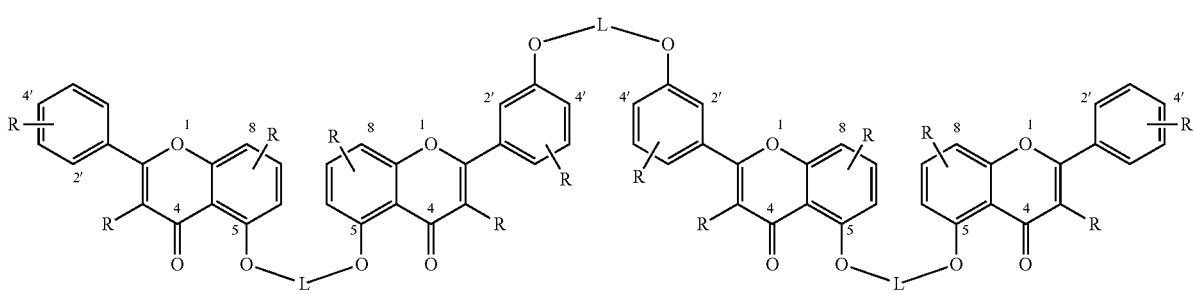

wherein

R is one or more of —OH, or —OSO$_3^-$M$^+$ or —H, each of which may be the same or different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

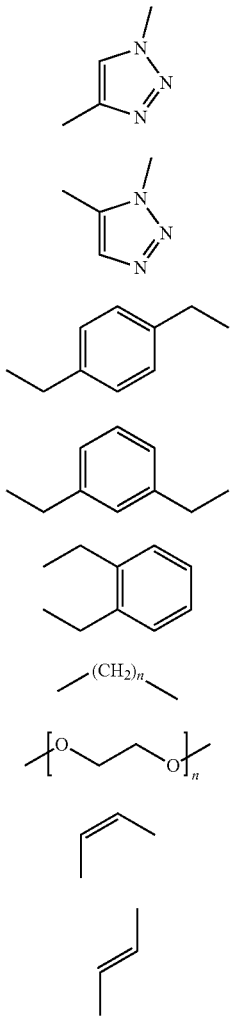

any two flavonoid units are connected through either 5-5, 5-6, 5-7, 5-8, 6-6, 6-7, 6-8, 7-7, 7-8, or 8-8 linkages.

The Examples below demonstrate that certain compounds have more functional activity in the practice of some of the methods of the claimed invention (for example, inhibition of CSCs) than other compounds, however, the less-functional compounds may be functional in the methods of the claimed invention upon modification of conditions such as dosage, formulation, or route of administration.

Exemplary methods of the invention involve identifying subjects or patients who might benefit from receiving therapy for cancer, such as colorectal cancer, through administration of at least one of the compounds described herein. Such subjects or patients are generally mammals, and usually humans, although this need not always be the case, since veterinary and research related applications of the technology are also contemplated. Generally a suitable subject or patient is identified by a health care professional or professionals using known tests, measurements, or criteria for either already having symptoms of cancer, for example colorectal cancer, or being at risk of developing cancer such as colorectal cancer. A suitable treatment protocol is then developed. The methods may also comprise one or more steps related to monitoring the effects or outcome of administration in order to evaluate the treatment protocol and/or to adjust the protocol as required or in a manner that is likely to provide more benefit, e.g. by increasing or decreasing doses of medication, or by changing the particular type of compound that is administered, or by changing the frequency of dosing or the route of administration, etc. While in some cases the improvement or lessening of symptoms (or the prevention of symptoms) that occurs may be complete, e.g. the functioning of the patient returns to or remains normal (as assessed in comparison to suitable control subjects or standardized values obtained therefrom), this need not always be the case. Those of skill in the art will recognize that even a lower level of improvement in symptoms may be highly beneficial to the patient, as may be the slowing of the progression or symptoms of the disease, even if a complete cure does not result.

The term "therapeutically effective amount" refers to an amount of a compound or composition effective to treat a disease or disorder, or they symptoms of said disease such as cancer in a subject. In the case of colorectal cancer or another cancer, the therapeutically effective amount of the compound or composition may reduce and/or prevent or slow the progression to some extent one or more of the symptoms associated with the cancer.

The methods of the invention involve administering pharmaceutical compositions comprising at least one (i.e. one or more) of the compound disclosed herein to a patient in need thereof. The present invention thus also provides compositions which comprise the compounds as described herein, usually together with a pharmacologically suitable carrier or diluent. In some embodiments, one substantially purified compound is present in a composition; in other embodiments more than one compound is present, each compound being substantially purified prior to being mixed in the composition. The preparation of pharmacologically suitable compositions for use as medicaments is well known to those of skill in the art. Typically, such compositions are prepared either as liquid solutions or suspensions, however solid dry forms such as tablets, pills, powders and the like are also contemplated. The liquid may be an aqueous liquid or oil. Solid forms suitable for solution in, or suspension in, liquids prior to administration may also be prepared. The preparation may also be emulsified. The active ingredients may be mixed with excipients or preservatives which are pharmaceutically acceptable and compatible with the active ingredients. Suitable excipients are, for example, water, saline, dextrose, glycerol, ethanol and the like, or combinations thereof. Exemplary preservatives may include parabens, etc. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of compound in the formulations may vary. However, in general, the amount in the formulations will be from about 1% to about 99%.

The compound compositions (preparations) of the present invention may be administered by any of the many suitable means which are well known to those of skill in the art, including but not limited to: by injection, inhalation, orally, intravaginally, intranasally, by ingestion of a food or product containing the mimic, topically, as eye drops, via sprays, etc. In exemplary embodiments, the mode of administration is orally or by injection. In addition, the compositions may be administered in conjunction with other treatment modalities such as other agents which are used to treat cancer or the conditions which cause cancer in the patient, examples of which include but are not limited to chemotherapy, radiation treatment, or anti-cancer drugs.

The amount of compound that is administered is generally in the range of from about 1 to about 200 mg/kg, e.g., from about 5 to about 20 mg/kg, etc., although as one of skill in the art will recognize, the precise amount may vary depending on one or more attributes of the drug recipient, including but not limited to: weight, overall health, gender, age, nationality, genetic history, other conditions being treated, etc., and the amount provided may be more or less than the range specified herein.

In some embodiments the compounds described herein are used prophylactically, e.g. they are administered to persons who have not yet exhibited symptoms of the disease but are deemed to be at risk for developing the disease (e.g. those who are known to have a genetic predisposition for cancer development), or simply those who are at risk due to other factors such as aging. The compounds may also be administered to individuals who are thought or deemed to be exhibiting early signs of disease or to be in early stages of disease. The compounds may also be administered to individuals who are known to have and who definitely exhibit symptoms of disease. Administration of the compounds described herein may prevent disease symptoms, may slow the progression of disease, and/or may reverse symptoms. Those of skill in the art will recognize that, while complete remission of disease may be desirable, great benefit may also accrue if partial remission or slowing of disease progress is achieved.

Other embodiments of the invention include the treatment of cancer, such as colorectal cancer, pancreatic cancer, or other epithelial cancers. These methods comprise the step of administering a therapeutically effective amount of at least one of the compounds of formula (I), formula (II), formula (III), formula (IV), formula (V), formula (VI), formula (VII), or formula (VIII) or a composition containing one or more of such compounds, with or without other cancer fighting agents, to a patient in need thereof to treat or prevent cancer. Examples of such cancers include, but are not limited to, breast cancer, prostate cancer, colon cancer, glioblastoma, endometrial cancer, lung cancer, thyroid cancer, lymphomas, ovarian cancer, or combinations thereof. In exemplary embodiments, the cancer to be treated is colorectal and pancreatic cancer.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE 1

Synthetic, Non-Saccharide, Glycosaminoglycan Mimetics Selectively Target Colon Cancer Stem Cells Introduction It was reasoned that a novel approach to target CSCs would be modulation of glycosaminoglycan (GAG) interactions with growth factors, cytokines or morphogens that play critical roles in CSC growth and/or differentiation. Signaling molecules shown to regulate CSCs include growth factors (e.g., fibroblast growth factors, transforming growth factor-β (TGF-β), bone morphogenetic proteins (BMPs)), cytokines (e.g., interleukins-6 and -8 (IL-6, IL-8)), or morphogens (e.g. Hedgehog (HH), Notch). These in turn influence many transcription factors including Nanog, Oct4 and SOX2 that play critical roles in deciding the fate of the stem cell (12). A majority of these factors interact with heparan sulfate (HS), a GAG that is increasingly being recognized as a regulator of stem cell growth. For example, an increase in the level of HS and its sulfation correlates with induction stem cell differentiation (13-15). Although the exact molecular mechanism of GAG action on stem cells remains unelucidated, one postulate is that different types of ternary complexes of HS with FGF-FGFR co-complex are formed, depending on the HS fine structure, that affect growth and/or differentiation (12). Another GAG that is an important component of CSC niche is hyaluronan (HA). This GAG interacts with CD44, which is a well-established CSC marker (16,17). Finally, chondroitin sulfate-containing proteoglycan, called CSPG4, is also present on CSCs and involved in binding to ECM proteins to regulate cell proliferation, migration and angiogenesis (18).

Structurally, GAGs are polymers of alternating hexosamine and hexuronic acid residues that are biosynthesized in the absence of a template through multiple enzymatic reactions. Thus, a cell's GAG population is structurally diverse (19), which may be modulated in a spatiotemporal manner through the action of sulfotransferases and sulfatases. Thus, it has been difficult to discover GAG-based therapeutics because their of relatively weak target selectivity and the difficulty of obtaining a library of homogenous GAG sequences for screening (20,21). It was hypothesized that GAG-protein interactions should be possible to effectively intercept or mimic using non-saccharide GAG mimetics (NSGMs), which are small, homogenous, aromatic molecules containing one or more sulfate groups (20,22). NSGMs are easy to synthesize, highly water soluble, and typically bind to proteins in a fairly selective manner, thereby affording a much higher level of selectivity than that possible with GAGs (23-26).

Recently, we developed a range of structurally unique, synthetic nonsaccharide GAG mimetics (NSGMs, see FIG. 1A for structures).[18,19] These novel molecules mimic GAG structure through appropriate placement of one or more sulfate group(s) on an aromatic scaffold. These NSGMs have been found to modulate several biological functions including coagulation, angiogenesis, inflammation and oxidation in which GAGs play important roles.[18] Thus, if a biological screen can be designed to exploit the difference(s) in growth characteristics between bulk cancer cells and CSCs, then novel synthetic NSGMs that selectively target CSCs should be possible to identify.

Figure 1B:
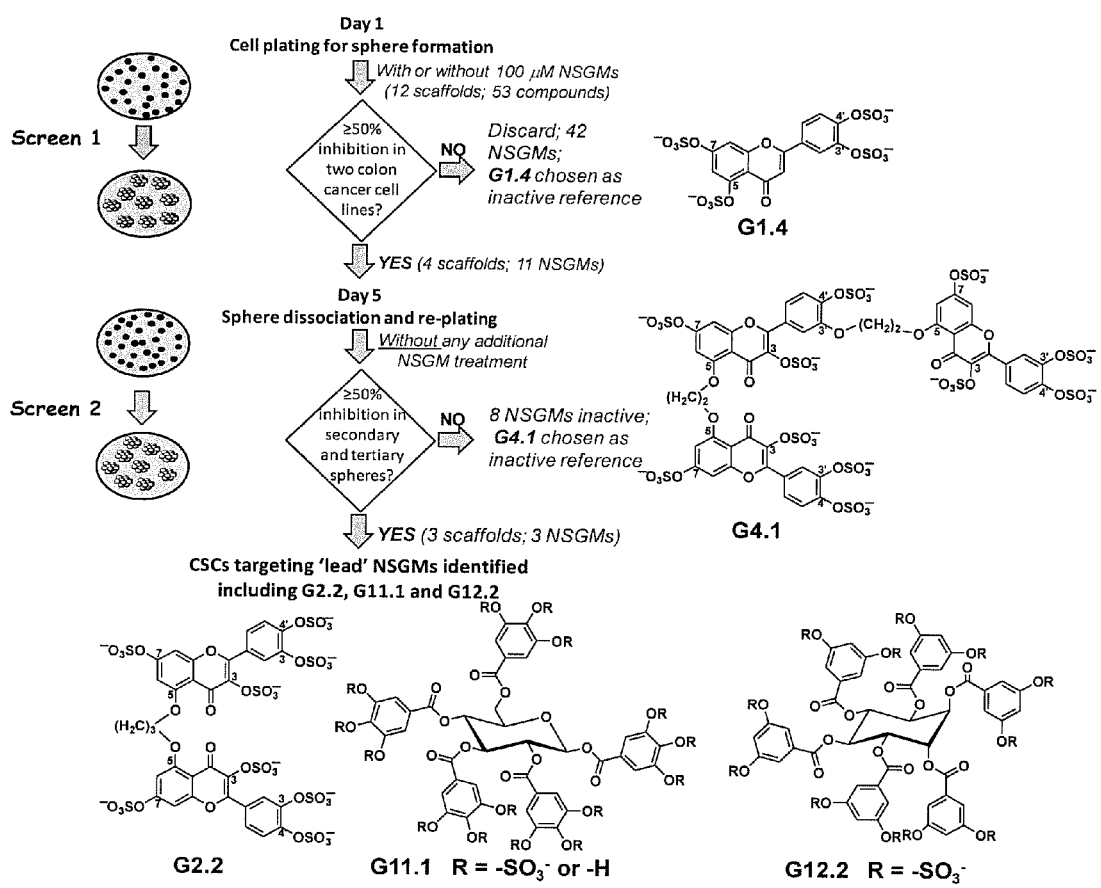

Herein, it is reported that screening a library of 53 novel, synthetic and homogenous NSGMs containing varying levels of sulfation and diverse aromatic scaffolds resulted in identification of three NSGMs, i.e., G2.2, G11.1 and G12.2, that selectively inhibit the growth and self-renewal properties of colorectal CSCs (FIG. 1B). The CSC inhibition activity was highly sensitive to the structure of the NSGM. For example, closely related analogs, G1.4 and G4.1, do not induce CSC inhibition. In the process, a novel tandem, dual screening strategy has been developed involving inhibition of monolayer versus spheroid growth and inhibition of primary (1°) versus secondary (2°) spheroid growth that can be very broadly applied for anti-cancer chemical biology and drug discovery. The identified NSGM down-regulated several CSC markers through regulation of gene transcription, while closely related, inactive NSGMs demonstrated no such changes. Moreover, the effects on CSCs were mediated, in part, through induction of apoptosis and inhibition of self-renewal factors. Thus, this work presents the paradigm that NSGMs (and GAGs) represent a rich, untapped avenue for modulation of CSCs.

Materials and Methods

Chemicals, Reagents and Chemical Methods. Anhydrous $CH_2Cl_2$, THF, $CH_3CN$, DMF, methanol, acetone and HPLC grade solvents were purchased from Sigma-Aldrich or Fisher and used as such. All other chemicals were of reaction grade as used as received from Sigma Aldrich, Fisher, or TCI America. n-Hexylamine for ion-pairing UPLC was from Acros Organics. Analytical TLC was performed using UNIPLATE™ silica gel GHLF 250 um pre-coated plates (ANALTECH). Column chromatography was performed using silica gel (200-400 mesh, 60 Å) from Sigma-Aldrich. Flash chromatography was performed using Teledyne ISCO, Combiflash RF system and disposable normal silica cartridges of 30-50μ particle size, 230-400 mesh size and 60 Å pore size. Sulfated molecules were purified using Sephadex G10 size exclusion chromatography. The quaternary ammonium counter ion of sulfate groups present in the molecules was exchanged for sodium ion using SP Sephadex-Na cation exchange chromatography. Each compound was characterized using $^1H$ and $^{13}C$ NMR spectroscopy, which was performed on Bruker 400 MHz spectrometer in either $CDCl_3$, $CD_3OD$, acetone-$d_6$, or $D_2O$. ESI MS of unsulfated molecules were recorded using Waters Acquity TQD MS spectrometer in positive ion mode, whereas ESI MS negative mode was used for sulfated compounds.

Synthesis and Characterization of Non-Saccharide Glycosaminoglycan Mimetics (NSGMs). The synthesis of G1.1-G1.7, G5.1-G5.2, G6.1-6.11, G7.1, G8.1, G9.1-9.2, G10.1-G10.8 and G11.1 has been reported earlier[19-25] and hence not presented here. NSGMs belonging to the G2, G3, G4, G11 (except for G11.1), and G12 scaffolds are new and are being reported for the first time. The detailed synthesis of these NSGMs (and intermediates used in their synthesis) is described in Examples 2-12. The synthetic protocol involves several steps of traditional organic chemistry transformations that typically yield good yields. Each new compound was characterized using $^1H$ and $^{13}C$ NMR spectroscopies on Bruker 400 MHz spectrometer and ESI-MS using Waters Acquity TQD MS spectrometer. The spectral data for newly synthesized molecules are presented in the Examples below.

Cell Culture. HT-29 and HCT-116 human colon cancer cells were obtained and PANC-1 cells were obtained from ATCC. These cells were maintained in 10 cm tissue cultured treated plate (USA Scientific) as monolayer in Dulbecco's Modified Eagle Medium: Nutrient Mixture F-12 (DMEM/F-12) (Gibco) supplemented with 10% fetal bovine serum (FBS) (Gibco), and 1% streptomycin/penicillin (AA) (Gibco). The cells were passaged using trypsin containing ethylenediaminetraacetic acid (EDTA) (Gibco) before they reached 70% confluence.

Cell Proliferation Assay. Cell proliferation was evaluated by (3-(4,5-dimethylthiazol-2-yl)-2,5-diphenyltetrazolium bromide) MTT cell proliferation assay. For HT-29 cell line approximately $2.5 \times 10^3$ cells/100 μL/well were plated in 96-well tissue culture treated plate. After overnight incubation at 37° C. vehicle (control) or NSGM was added at the desired concentration and the cells were further incubated for 60-72 h. At the end of the incubation, 10 μL of 5 mg/mL MTT solution (Sigma) made in phosphate buffered saline (PBS) (Gibco) was added to each well and incubated for minimum of 2 to 3 hr until crystals formation was observed. Following this, 150 μL of 4 mM HCl (Sigma) in isopropanol solution was added drop wise to each well and the mixture was triturated until the crystals dissolve completely. Finally, the plate was placed on the spectrophotometer reader and read at 590 nm and growth inhibition was calculated as percent of control.

Primary (1°) Colonosphere Formation Assay. For primary sphere formation, cells were plated in non-treated, low adhesion, 96 wells plate at the concentration of 100 cells/100 μL/well in stem cell media (SCM) that consisted of DMEM:F12:AA (Gibco), supplemented with 1×B27 (Gibco), 20 ng/mL epidermal growth factor and 10 ng/mL fibroblast growth factor (Sigma). After four hour of incubation, vehicle (control) or NSGM at the desired concentrations were added to each well (at least in triplicates for each sample). On day five, numbers of spheres ranging from 50-150 mm in diameter were counted using phase contrast microscope and percent inhibition was calculated compared to control.

Secondary (2°) and Tertiary (3°) Colonosphere Assay. For secondary colonospheres, the 96-well plate of primary spheres was centrifuged at speed of 1000 rpm for 1 min and the supernatant was removed. Spheres that settled at the base of the plate were trypsinized with 20 μL/well and single cell suspension was prepared using vigorous mechanical dissociation. The numbers of viable cell were counted with 1:5 ratio of cell:trypan blue and then re-plated at 100 cells/100 mL/well in SCM media in a low adhesion plate. No further treatment with NSGMs was performed. Numbers of spheres were counted as above on day 5. The same method was repeated for tertiary spheres.

Western Blotting Analysis. Western blot analysis was performed according to the standard protocol described in the literature. Briefly, HT-29 cells were plated in serum-free SCM in a low adhesion 6-well plate to obtain spheroids. Mature spheroids were treated on day 4 after plating, with vehicle or NSGMs for indicated time and cells were solubilized in lysis buffer (20 mM $Na_3PO_4$, 100 mM NaCl, 2 mM EDTA, 1% Nonidet P-40, 2.5 mM $Na_3VO_4$) containing protease (Roche) as well as phosphatase inhibitor cocktails (Sigma). Following centrifugation at 14,000 g for 15 min, the supernatant was used for Western blot analysis. In all analyses, protein concentration was determined by the Bio-Rad Protein Assay kit (Bio-Rad). Approximately 25-50 μg of protein was separated by polyacrylamide gel electrophoresis and was transferred to PVDF membrane (Bio-Rad). Blocking was done with 5% low fat milk powder for 1 hr followed by overnight incubation with primary antibody (dilution 1:1000): anti-CD44 (Cell Signaling), anti-EpCAM (Cell Signaling), anti-LGR5 (Origene), anti-CD133 ((Miltenyi Biotec), anti-CXCR4 (Abeam), anti-OCT4 (Cell Signaling), anti-BMI-1 (Millipore), anti-c-MYC (Millipore) and anti-CK20 (Abeam). This was followed by incubation with appropriate secondary antibody and protein bands were visualized using the enhanced chemiluminescence detection system and imaged with LAS-3000 Imaging System (FUJIFILM). Densitometry was determined by AIDA image analyzer software (Raytest) and results were calculated as relative intensity compared to control. All experiments were performed at least three times.

Flow Cytometry Analysis. Human colon cancer HT-29 cells, grown in spheroid or monolayer condition were treated with vehicle or NSGMs for 24 hours, were trypsinized and single cells were re-suspended at $10^6$ cells/mL in PBS buffer. Cells were incubated with fluorophore conjugated antibody for 30 minutes at 4° C. and washed once with PBS buffer prior to analysis. Following antibody and dilution were used: LGR5-PE) (Dilution 1:50, Origene), DCLK1 (Dilution 1:33, Abeam). Cell sorting was performed using FACSAria™ II High-Speed Cell Sorter (BD Biosciences) and data were analyzed with FCS Express 4 Flow Cytometry software (De-Novo Software).

Real-Time PCR Analysis. Total RNA was isolated using the mirVana™ miRNA Isolation Kit (Life technologies, Grand Island, N.Y.). 1 μg total RNA was reverse transcribed using First-Strand cDNA Synthesis Kit using hexamer reverse primer (Affymetrix). Real time QPCR was performed using $RT^2$ SYBR® Green qPCR Master mix (Qiagen) in a 7500 fast real time machine (Applied Biosystem). Relative expressions of mRNA were calculated using ΔΔCT methods using GAPDH as a loading control.

Differentiation Assay. Single cell suspension from mature HT-29 colonosphere pre-treated with vehicle or G2.2 for 24 hours were plated on collagen coated glass cover slips or flasks in the presence of media supplemented with 2.5% FBS containing G2.2 or vehicle. At indicated time points, cells lysate was examined for CK-20 expression with western-blot as above. Alternatively, cells were fixed with 4% paraformaldehyde for 20 minutes at room temperature, permeabilized for 5 min in 0.5% Triton X-100 solution and blocked in PBS containing 1% BSA for one hour prior to incubation with anti-CK-20 antibody (Abeam) for 2 hours. Cells were then washed, incubated for 60 min with Alexa Fluor conjugate secondary antibodies, rinsed with blocking buffer and mounted on slides with DAPI containing ProLong® Gold Antifade Reagent (Invitrogen). Fluorescently labeled cells were examined using a Zeiss LSM700 laser scanning confocal microscope (Zeiss Micro imaging Inc.). Alexa Flour® 555 signals were imaged sequentially at 40× magnification in frame-interlaced mode to eliminate cross talk between channels.

Apoptosis Assay. Human colon cancer HCT-116 cells, grown in spheroid condition were treated with vehicle or NSGMs for 24 hours. Following which cells were trypsinized and single cells were re-suspended at $10^6$ cells/mL in PBS buffer. Two different methods were used to assess apoptosis induction. In the first methods, cells were incubated with propidium iodide and Annexin V-APC (ebioscience) and flow cytometric analyses were performed as above. In the second method, fluorescence microscopy was employed to examine morphological changes suggestive of apoptosis following staining with 1:1 mixture of 100 μg/ml each of acridine orange (AO) and ethidium bromide (EB) prepared in PBS. Briefly, a small volume of cell suspension was mounted on a glass slide and incubated with 1 μl of AO/EB solution and mixed gently just prior to microscopy and quantification. At least 500 cells in 10-15 fields were examined in each sample using Nikon ECLIPSE E800M fluorescence microscope using 20× objective. Results were quantitated as proportion of cells exhibiting characteristic apoptotic morphology normalized to vehicle treated controls. The data was expressed as apoptosis index=[([apoptotic cells (NSGMs)/total cells (NSGMs)]/[apoptotic cells (vehicle)/total cells (vehicle)]).

Statistical Analysis. All data are expressed as means±SEM unless otherwise indicated. The results were analyzed using the unpaired, two-tailed Student's Mest. $P < 0.01$ was designated as the level of significance unless specified otherwise.

Results and Discussion

Rationale, Design and Synthesis of Non-Saccharide GAG Mimetics Library: Structurally, GAGs are polymers of alternating hexosamine and hexuronic acid residues that are variably sulfated resulting in a natural library of millions of sequences The core polysaccharide scaffold primarily orients key sulfate groups in three-dimensional space for optimal interaction with the target protein.[18,20] Sulfated NSGMs attempt to exploit this concept of functional mimicry through sulfate group recognition. In fact, this concept has led to the design of sulfated flavonoids[20,21] and sulfated tetrahydroisoquinolines[22] as mimetics of a specific sequence in heparin using computational techniques. Likewise, sulfated quinazolinones,[23] sulfated benzofurans,[24] and sulfated gallolylglucopyranoses[25] have also been developed as effective mimetics of GAGs. These small, synthetic, homogeneous molecules bind in the GAG-binding site of proteins resulting in modulation of function.[20-25] This function could be either agonistic or antagonistic. For example, sulfated tetrahydroisoquinolines mimic the interaction of heparin with antithrombin and thereby generate agonistic effect.[22] In contrast, sulfated benzofurans introduce hydrophobic as well as electrostatic interactions and result in an antagonistic effect.[24]

Taking into account the role of GAGs in CSC growth and differentiation, it was predicted that a distinct NSGM may selectively target colorectal CSCs. Hence, a small library of sulfated NSGMs was selected for screening (FIG. 1A). As a group, the library represented twelve distinct scaffolds, G1 through G12, and 53 unique molecules possessing one to thirteen sulfate groups, linear length of ~8-24 Å and a range of three-dimensional shape from approximately planar (G1 scaffold) to globular (G12). Except for the G2-G4 scaffolds, the synthesis of other scaffolds has been reported.[19-25] We report here the synthesis of G2-G4 NSGMs (see below Examples for synthesis schemes). The synthesis of these molecules exploited the differential reactivity of the 5- and 3'-phenolic groups present on quercetin arising from the differential intramolecular hydrogen bonding. The differentially protected quercetins could then be site-selectively coupled to afford either G2 (5-5 coupling) or G3 mimetics (3'-3' coupling) in high yields. Extension of this technique further led to the synthesis of G4 group of NSGMs by coupling G2 with the G1 scaffold. The final step is sulfation of the polyphenolic precursor using trialkylamine-sulfur trioxide complex under microwave conditions[26]. It is important to note that the synthetic strategy developed here provides novel variably sulfated molecules in high yields and high homogeneity (>95% purity).

Figure 2A:
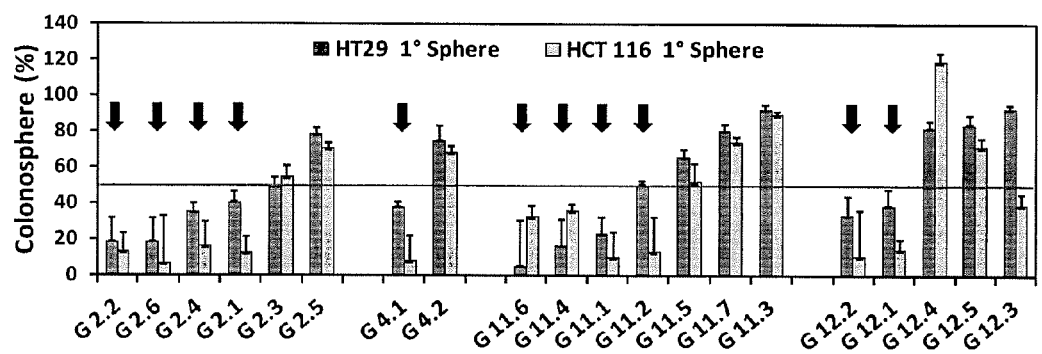
FIG. 2A-B. Results of the tandem, dual screening strategy. (A) Screen 1 results following primary spheroid growth studies in two colon cancer cell lines HCT-116 (p53 wild type, K-RAS mutant, microsatellite instable) and HT-29 (p53 mutant, K-RAS wild type, microsatellite stable). The 20 NSGMs identified for this study were at 100 µM concentration. (B) Screen 2 (secondary (2°) and tertiary (3°) growth assays) results with hits identified in Screen 1. Note: NSGMs were not added to the medium in 2° and 3° growth assays. Arrows indicate positive hits in Screen 1 (A) and Screen 2 (B) (p-value <0.0005). Data is represented as percent of vehicle-treated cells. Error bars represent ±1 SEM.

Identification of Sulfated NSGMs that Inhibit Growth and Self-Renewal of CSCs: To study the CSC-targeting ability of the sulfated NSGMs, the earlier observation that CSCs/progenitors are enhanced several-fold in spheroid culture compared to monolayer culture was used.[27] In fact, colon HT-29 spheroids were found to express Leu-rich repeat-containing G-protein coupled receptor 5 (LGR5), an established CSC marker,[28] several-fold higher than cells grown as monolayers. More importantly, CSCs grown in spheroid condition differ significantly from monolayer counterparts with respect to activation of key signaling pathways, e.g., Wnt/β-catenin signaling among others.[16,27] We exploited this to develop a novel screen for identifying molecules that selectively target colorectal CSCs. In this screen, sulfated NSGMs that inhibit HT-29 growth under spheroid conditions, but not under monolayer conditions, were then assessed for retention of 2° and 3° spheroid growth inhibition profiles in the absence of NSGM. The latter screen is of particular importance as primary spheroid growth although selective for CSCs doses not distinguish between non self-renewing progenitors and self-renewing CSCs. Hence, sulfated NSGMs that satisfy this tandem, dual screen would preferentially target self-renewing CSCs. From the library of 53 sulfated NSGMs, 11 showed >50% inhibition of primary sphere formation in HT-29 cells (FIG. 2A-B) without inducing any meaningful inhibition of monolayer growth. These 11 NSGMs belonged to G2, G4, G11 and G12 scaffolds but only four of the six G2 molecules, one of the two G4, four of the seven G11 and two of the five G12 molecules satisfied the first screen. Similar results were observed for HCT-116 colon cancer cell line (FIG. 2A), which has a distinct genetic background compared to HT-29 cells. Interestingly, the active G2 and G4 NSGMs showed better inhibition of HCT-116 CSCs (p53 wild-type) as compared to HT-29 spheroids (p53 mutant). In contrast, G11 and G12 NSGMs did not display such a consistent trend.

Figure 2B:
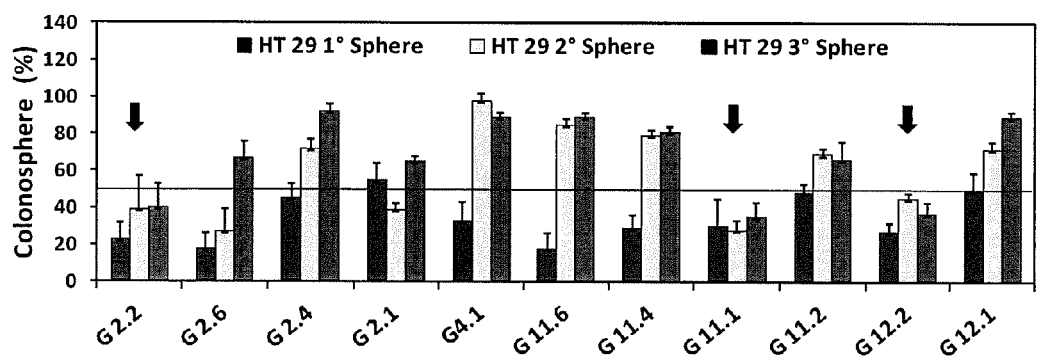

The 11 sulfated NSGMs were then studied for their effect on 2° and 3° sphere formation (HT-29 and HCT-116) in Screen 2. By design, this screen reflects a test of true self-renewability of CSCs.[2,3] Single cell suspension obtained from primary spheres formed above was then cultured in the absence of NSGM. Only three (G2.2, G11.1 and G12.2) showed >50% inhibition in both 2° and 3° sphere formation in HT-29 cells (FIG. 2B). Of these three, G2.2 (a dimeric sulfated flavonoid) was especially interesting because two closely related analogs, G1.4 (monomelic) and G4.1 (trimeric), completely failed at Screen 1 and Screen 2 stages, respectively (FIG. 1B). G2.2, the 'lead' NSGM demonstrated a steep dose-response profile for primary spheroid inhibition with an apparent $IC_{50}$ of ~58 µM. Moreover, G2.2 also inhibited spheroid formation in HCT-116 (p53 null) and Panc-1 (pancreatic) cancer cell lines with essentially identical potency. The results suggested a more generic applicability of CSC-targeting effect of G2.2.

Figure 3A:
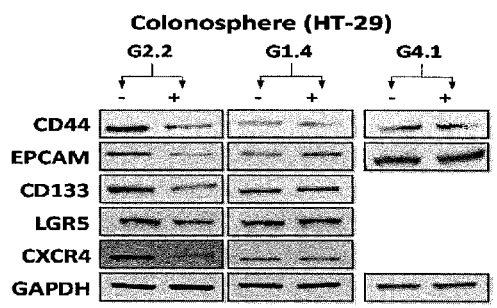
FIG. 3A-D. Effects of G2.2 and its inactive structural analogs, G1.4 and G4.1, on CSC markers. (A and B) shows the effect on the protein expression of CSC markers including CD44, EpCAM, CD133, LGR5 and CXCR4, while (C) shows flow cytometry profiles of LGR5, a CSC marker, expression in spheroids treated with G2.2 (100 µM) or its analogs (100 µM) as compared to vehicle-treated cells. (D) shows the results of treatment with known pharmacological activator (GSK-3P inhibitor, CHIR-99021 (100 nM)) and inhibitor (iCRT14 (40 nM)) of β-catenin pathway, which regulates LGR5 expression, were used as biological control to establish appropriate gating for analyses of flow data (C). Western blots (A) were performed using antibodies available for the studied CSC markers. GAPDH is the house-keeping control. Bar graphs (B) show the relative change in expression levels of the marker in comparison to vehicle-treated CSCs using densitometry. Error bars represent ±1 SEM. *represents p<0.01 compared to respective controls.
Figure 3B:
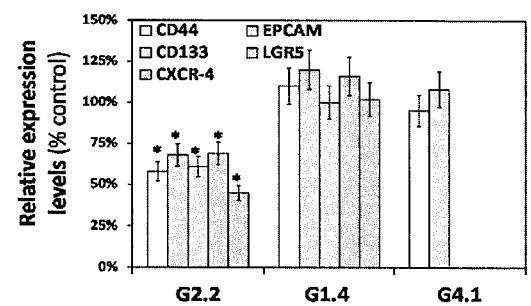
Figure 3C:
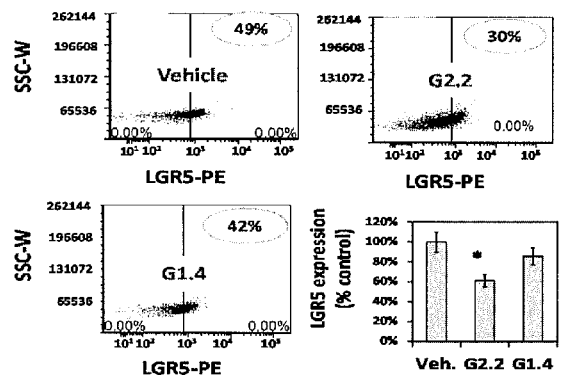
Figure 3D:
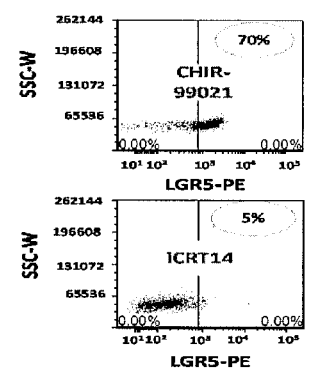

G2.2 Induces Distinct Molecular Changes Supporting Phenotypic Effects: As predicted on the basis of results achieved in the selective targeting assay, G2.2 inhibited expression of CSCs markers and self-renewal factors in HT-29 colon cancer cells confirming its CSC-targeting ability. G2.2 reduced the expression of all five CSCs markers[28,29] examined including CD44, CD133, epithelial adhesion molecule (EpCAM), LGR5, C-X-C chemokine receptor type 4 (CXCR-4) by ~25-55% (FIGS. 3a and 3b). In striking contrast, G1.4 and G4.1 displayed no effect on the expression of any of the CSCs markers tested (FIGS. 3a and 3b). Additionally, flow-cytometric analyses for LGR5 showed a similar (39%) reduction in LGR5 (hi) cells following treatment with G2.2, but only a modest (<15%) decrease with G1.4 compared to vehicle-treated controls (FIG. 3c). To confirm that these changes are meaningful, we performed two control experiments with agents known to up- or down-regulate LGR5. Considering that LGR5 is a target of canonical β-catenin signaling,[30] exposure to an activator (GSK-3β inhibitor CHIR-99021)[31] or inhibitor (iCRT14)[32] of β-catenin signaling should predictably alter expression of LGR5. FIG. 3d results confirm these predictions and further support the phenotypic changes induced by G2.2. Likewise, similar findings were observed for DCLK1, another intestinal stem cell marker that is highly expressed in colon CSCs[33].

To understand the mechanism by which G2.2 might induce these molecular changes, the expression of above CSC markers at mRNA and protein levels at various time points was examined. A marked decrease in mRNA levels was observed of several CSC markers at 6 hours following treatment with G2.2 compared to controls (FIG. 4a). With regard to the corresponding proteins, there was minimal change at 6 hours but a significant decrease at 24 hours (FIG. 4b). These findings suggest that mRNA changes precede changes in protein expression strongly supporting the notion that G2.2 regulates CSC markers through regulation of gene transcription. Taken together, these results provide compelling evidence that G2.2 targets CSCs at a molecular level, which supports the phenotypic findings of spheroid growth inhibition described above. More importantly, the structure-activity dependence observed between two related NSGMs suggest that the fine structure of the molecule is critical for the CSC targeting ability.

Figure 5A:
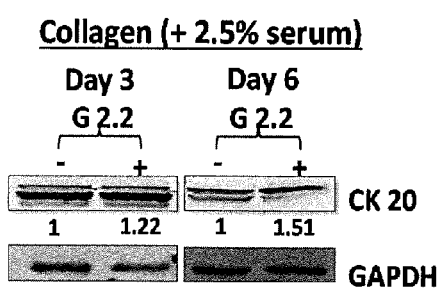
FIG. 5A-D. Mechanisms of CSC targeting by G2.2. (A & B) Expression of colonic differentiation marker CK20 in colonosphere cells at various time points using Western-blot (A) and immuno cytochemistry and imaged with confocal microscopy (B). Differentiation was induced by growing the cells on collagen matrix in the presence of 2.5% serum. (C & D) The effect on the expression of self-renewal factors including OCT4, BMI-1 and C-MYC. Bar graphs (D) show the relative change in expression levels of the marker in comparison to vehicle-treated CSCs using densitometry. NSGM treatment was carried out at 100 μM concentration. Error bars represent ±1 SEM. * represents p<0.01 compared to respective controls. The experiments were carried out in HT-29 colon cancer cells.
Figure 5B:
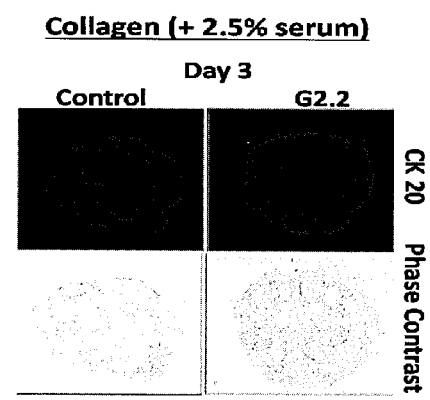
Figure 5C:
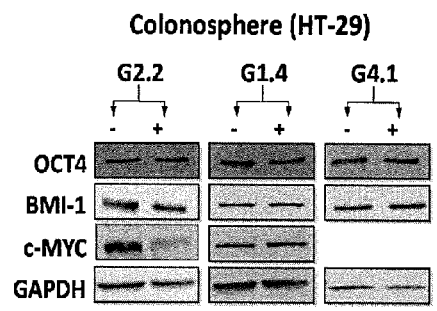
Figure 5D:
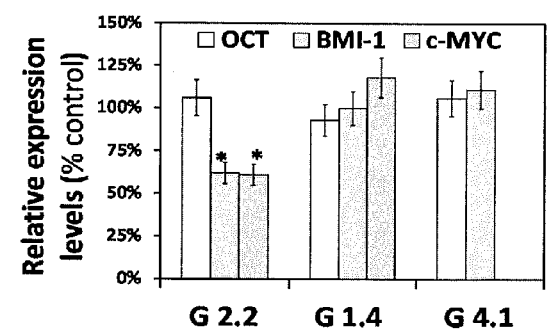

Mechanism of G2.2 Mediated Inhibition of CSC Growth: To gain further insight into mechanism of selective CSC targeting by G2.2, its effect on broad cellular processes in spheroid cells was examined. CSC growth is regulated by a fine balance between self-renewal and differentiation.[34] CK20, a marker of colonic differentiation, expression was examined in spheroid cells grown on collagen in the presence of 2.5% serum, which is known to promote differentiation,[16] following treatment with G2.2. Only a modest induction of CK20 expression was observed following G2.2 treatment compared to vehicle treated controls using two different methods (Western blot and immunocytochemistry, FIGS. 5a and 5b). On the other hand, G2.2 caused a significant inhibition of self-renewal factors BMI-1 and c-MYC, while it had little effect on OCT-4 levels (FIGS. 5c and 5d). In comparison, the inactive analog G1.4 induced no such changes (FIGS. 5c and 5d). These findings suggest that G2.2 might inhibit CSC growth, at least in part, through attenuation of self-renewal. In fact, inhibition of BMI-1 expression in colon cancer is being currently exploited as a therapeutic strategy to selectively target CSCs.[35]

Figure 6A:
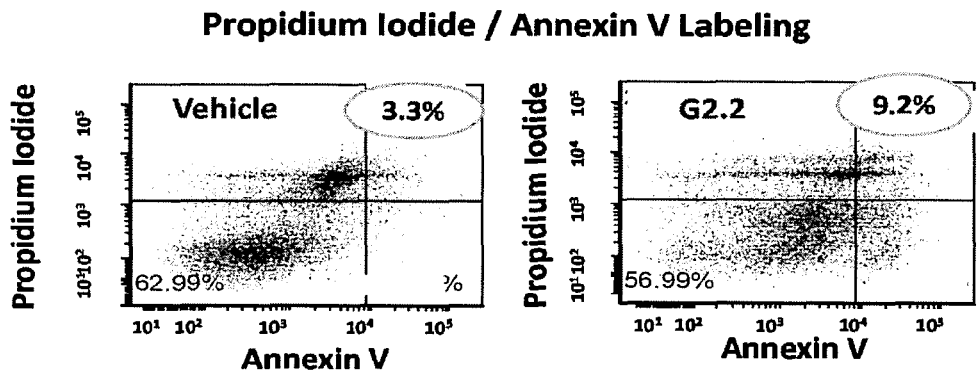
FIG. 6A-C. Mechanisms of CSC targeting by G2.2. (A & B) Apoptosis induction was measured as proportion of annexin V (+)/propidium iodide (+) cells (A) and as relative proportion of cells exhibiting nuclear changes characteristic of apoptosis using fluorescence microscopy following staining with acridine orange and ethidium bromide dyes (B). Apoptosis index=([apoptotic cells (exp.)/total cells (exp.)]/ [apoptotic cells (ctr.)/total cells (ctr.)]). (C) Shows relative cell cycle distribution at 24 hours following appropriate treatment. Treatment with respective NSGM (100 μM) was carried out in HT-29 colon cancer cells. Error bars represent ±1 SEM. * represents p<0.01 compared to respective controls.
Figure 6B:
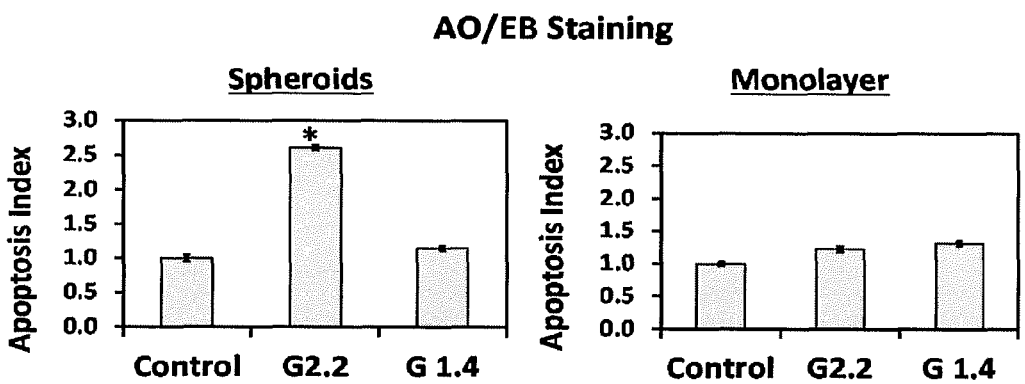
Figure 6C:
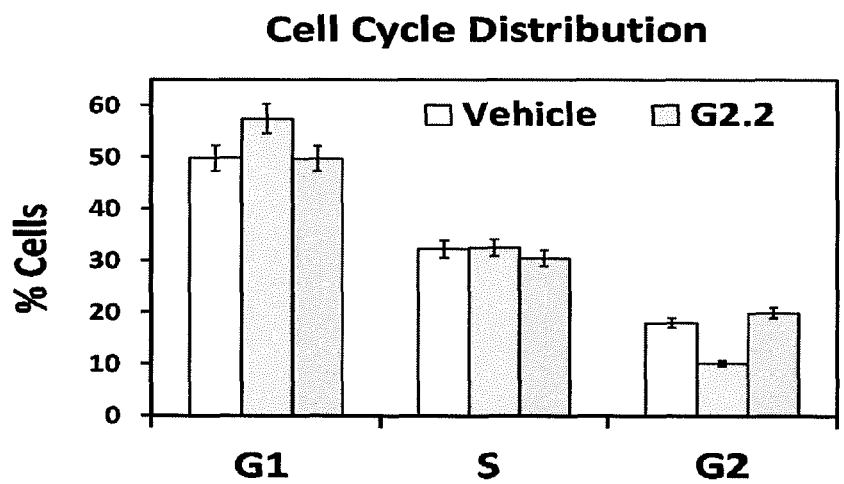

To understand if G2.2 might exert additional effects on growth/survival of CSCs, we examined cell cycle distribution as well as induction of apoptosis in spheroid cells. G2.2 caused a very modest effect on cell cycle progression as evident by the small increase in proportion of spheroid cells in G1 phase compared to vehicle treated controls (FIGS. 6a-b). On the other hand, using two different methods to examine apoptosis induction, annexin V labeling and acridine orange/ethidium bromide staining, we observed a 2 to 3-fold induction of apoptosis in spheroid cells treated with G2.2 compared to vehicle treated controls (FIGS. 6a and 6b). In contrast, the inactive analog G1.4 demonstrated no such effects (FIG. 6b). Moreover, G2.2 did not induce apoptosis in CSC-poor monolayer counterparts (FIG. 6b). Overall, the findings suggest that G2.2 selectively inhibits CSCs through induction of apoptosis as well as attenuation of self-renewal.

CONCLUSIONS

This is the first study describing anti-colon CSC selective properties of a NSGM. These molecules represent a major translational advance over naturally occurring GAGs because of their ease of synthesis, biophysical properties (hydrophobic as well as hydrophilic nature) and structural homogeneity.[18] In fact, the structural complexity of GAGs has been a major challenge and NSGMs are likely to fulfill the major gap in availability of GAG-like molecules.

The therapeutic and chemical biology potential of NSGMs and GAG-like molecules is high. PI-88, a mixture of highly sulfated oligomannans that targets growth factor signaling, is being currently evaluated in clinical trials of various cancers.[36,37] However, it is not known whether PI-88 targets CSCs. NSGMs also possesses multiple sulfate groups, in the manner of PI-88, and earlier work shows that they typically bind in the GAG-binding site on proteins and modulate function.[18-23] The fine structure-activity relationship noted in the anti-CSC function of NSGMs suggests recognition of one or more target protein(s). One important finding of this work is that G2.2 inhibits CSCs from several cell lines (HT-29, HCT-116 & Panc-1). This implies that a broader anti-CSC profile is possible through NSGMs.

Finally, the tandem, dual screen approach opens up a novel and relatively simple avenue for not only discovering anti-CSC agents but also identifying agents selectively targeting progenitor cells. In fact, such an observation is discussed with G4.1. Although G4.1 belongs to the same core scaffold as G2.2 (the flavonoid scaffold), it exerts its effects mostly on early progenitor cells. This finding implies that microscopic configurational and/or conformational differences play key roles in fine tuning selectivity for targeting CSCs or progenitor cells. Such structural dependence of biological activity for NSGMs has been observed earlier and highlights the functionality of using this approach for advancing fundamental functional understanding of stem cells/progenitors biology using chemical tools.

EXAMPLE 2

Synthesis of Protected Quercetin

Figure 7:
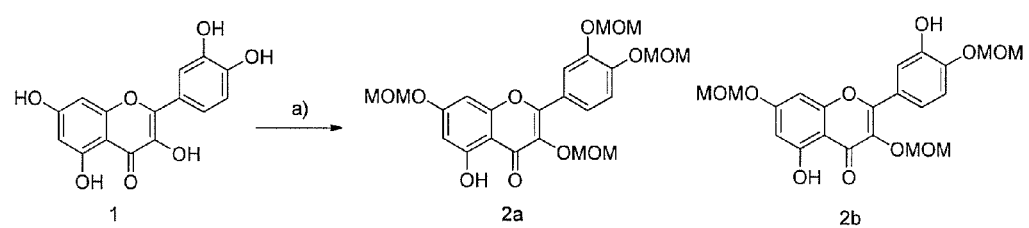
FIG. 7. Protection of Quercetin. Illustrated is the protection of quercetin (compound 1) using methoxy methyl chloride as a protecting group giving two products 3, 7, 4'-tri- and 3, 7, 3', 4'-O-tetra methoxy methylated quercetin (compounds 2a and 2b respectively), a) MOMCl, DCM, N, N'-diisopropylethylamine, rt/overnight, 65-70% overall yield.

The protection of quercetin using methoxy methyl chloride as a protecting group giving two products 3, 7, 4'-tri- and 3, 7, 3', 4'-O-tetra methoxy methylated quercetin (FIG. 7). General Procedure for Protection: To a solution of quercetin (1.0 equiv) in DCM, N, N-diisopropylethylamine (8.0 equiv) and MOM chloride (3.5 equiv) was added under nitrogen. After vigorous stirring at 0° C. for 1 h, the reaction mixture was allowed to warm to room temperature over 2 h and the stirring was maintained for 12 h. The resulting mixture was diluted with water (100 ml), extracted with EtOAC (200 ml), and then the organic layer was washed with water (100 ml) and dried over $NaSO_4$. The residue obtained after removal of the solvent was purified by flash column chromatography to afford two products: the tri protected ether 2a (50% yield) and tetra protected ether 2b (50% yield).

EXAMPLE 3

Synthesis of Protected 5, 5-O Flavonoid Dimers 3-8

Figure 8:
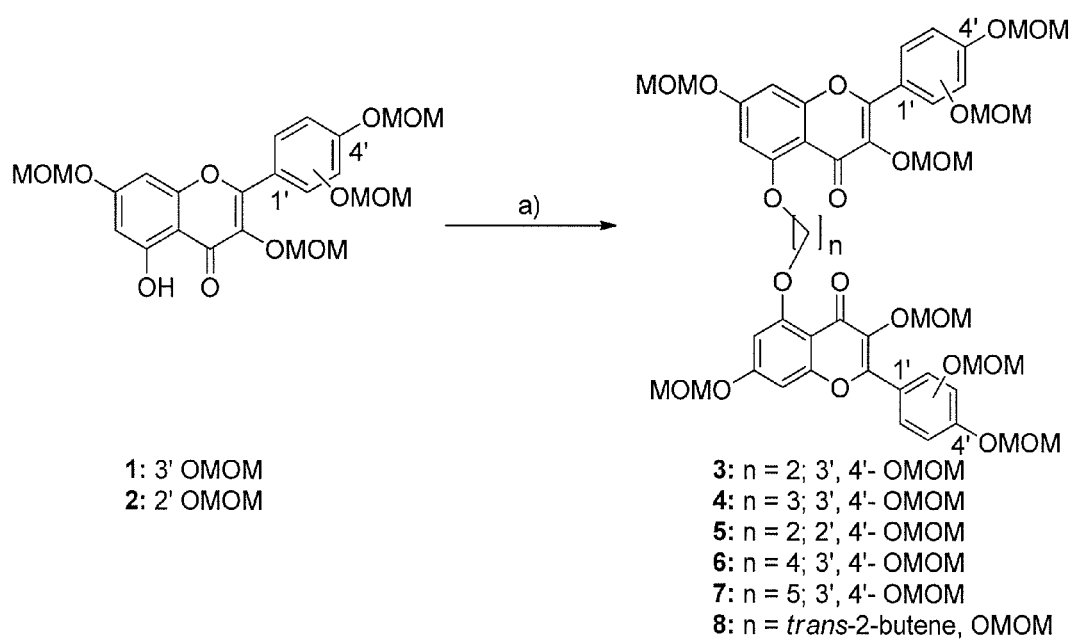
FIG. 8. Synthesis of protected 5, 5-O flavonoid dimers 3-8: a) $K_2CO_3$, dibromoalkane (0.5 equiv), DMF, rt/12 h, 85-90%.

General Procedure for Synthesis of Protected 5, 5-O Flavonoid Dimers (FIG. 8): To a solution of 1 or 2 (1.0 equiv) in N, N-dimethylformamide was added $K_2CO_3$ (2.5 equiv) and stirred for two minutes. This was followed by addition of dibromoalkane (0.5 equiv) and stirred vigorously for 12 hours. After the reaction completed as indicated from TLC the reaction mixture was diluted with EtOAC (25 mL) and water (25 mL). The organic layer was separated and the aqueous phase was extracted with EtOAc (2×25 mL), organic layer was washed with saturated NaCl solution (25 mL). The combined organic layers were dried over anhydrous $Na_2SO_4$, evaporated under reduced pressure to afford crude compounds 3-8, which were further purified using flash chromatography on silica gel (70-85% ethyl acetate in hexanes).

EXAMPLE 4

Synthesis of Polyphenoiic 5, 5-O Flavonoid Dimers 3a-8a

Figure 9:
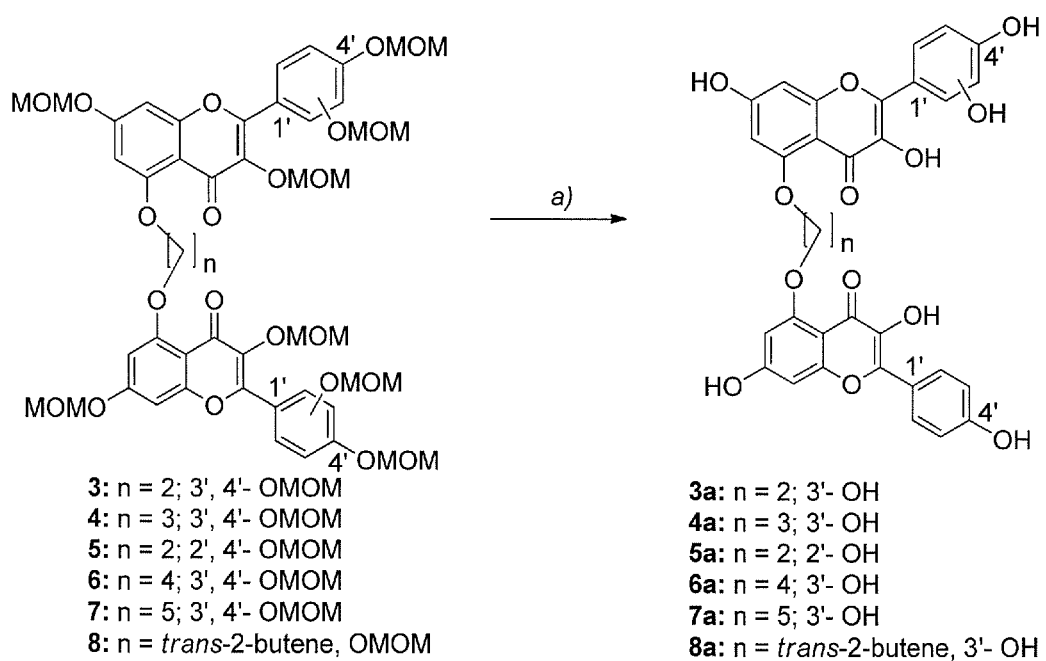
FIG. 9. Synthesis of polyphenol 5, 5-O-flavonoid dimers 3a-8a: a) p-toluenesulfonic acid, MeOH, reflux/48 h, 55-65%.

General Procedure for Synthesis of Polyphenolic 5, 5-O Flavonoid Dimers (FIG. 9): The methoxy methyl groups present in the compounds 3-8 were completely deprotected using following procedure. To a solution of methoxy methylated compound 3-8 in methanol was taken in a flask attached to a reflux condenser and p-toluenesulfonic acid (catalytic) was added to it. The reaction mixture was stirred at reflux temperature, the extent of deprotection was monitored using UPLC-MS and continued until complete deprotection of all MOM groups. After completion of the reaction EtOAC (25 mL) was added to precipitate the mixture. The precipitate was filtered, washed with excess EtOAC to remove p-toluenesulfonic acid and dried to obtain pure polyphenolic compounds 3a-8a.

EXAMPLE 5

Synthesis of Sulfated 5, 5-O Flavonoid Dimers G2.1-G2.6

Figure 10:
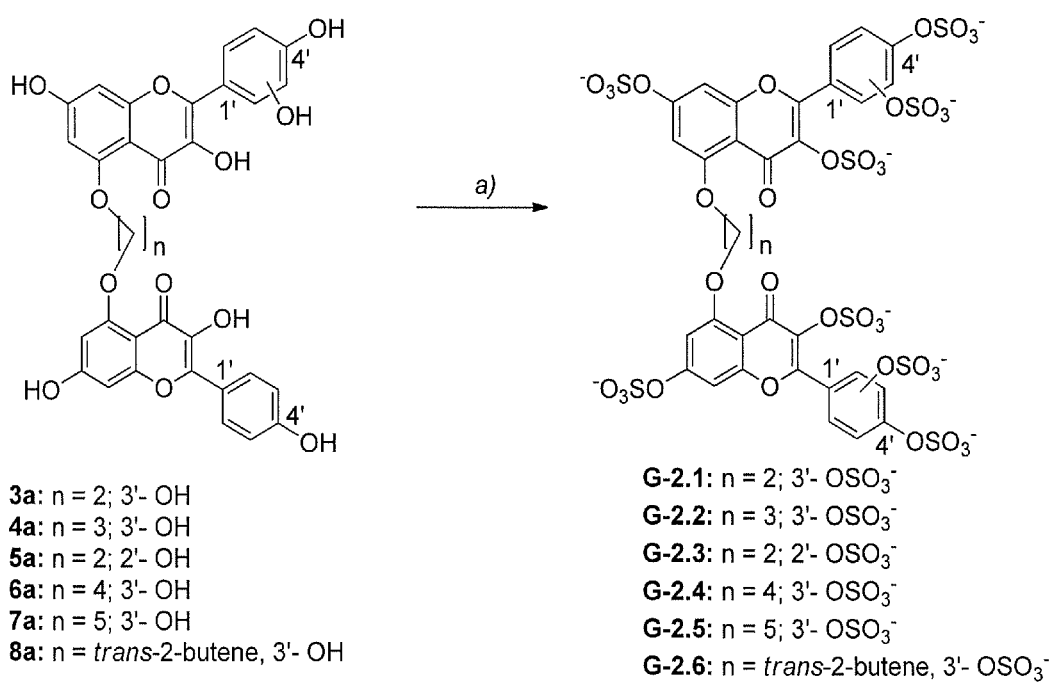
FIG. 10. Synthesis of sulfated 5,5-O-flavonoid dimers G2.1-G2.6: a) $SO_3$:$Me_3N$, $Et_3N$, $CH_3CN$, microwave/6 h, 75-85%.

General Procedure for Synthesis of Sulfated 5, 5-O Flavonoid Dimers (FIG. 10): Sulfation of phenolic precursors was achieved using microwave-assisted chemical sulfation as described earlier[1,2]. Briefly, to a stirred solution of polyphenol in anhydrous $CH_3CN$ (1-5 mL) at room temperature, $Et_3N$ (10 equiv per —OH group) and $Me_3N/SO_3$ complex (6 equiv per —OH) were added. The reaction vessel was sealed and microwaved (CEM Discover, Cary, N.C.) for 6 to 8 h at 90° C. The reaction mixture was cooled and transferred to a roundbottom flask, and the volume was reduced as much as possible under low pressure conditions at 25° C. The reaction mixture was then directly loaded on to a flash chromatography column and purified using a dichloromethane and methanol solvent system (5-30%) to obtain the sulfated flavonoid dimers and trimers. The samples were concentrated and reloaded onto a SP Sephadex C-25 column for sodium exchange. Appropriate fractions were pooled, concentrated in vacuo, and lyophilized to obtain a white powder. Spectral characteristics of all the sulfated compounds G2.1-G2.6 are listed below.

G2.1. $^1$H NMR (DMSO-$d_6$, 400 MHz): 8.19-8.09 (m, 4 H), 7.66 (d, J=9 Hz, 2 H), 7.1 (d, J=2 Hz, 2 H), 6.87 (d, J=2.0 Hz, 2 H), 4.55 (s, 4 H). $^{13}$C NMR (DMSO-$d_6$, 100 MHz): 174.14, 158.66, 156.91, 154.16, 146.72, 142.98, 135.13, 124.6, 123.27, 119.90, 118.83, 109.70, 99.78, 68.21. ESI-MS calculated for $C_{32}H_{14}Na_8O_{38}S_8$ [(M+Na)]$^+$, m/z 1469.87, found [(M−8Na+8 HxA)+2HxA]$^{2+}$, m/z 1142.812.

G2.2. $^1$H NMR (DMSO-$d_6$, 400 MHz): 8.07-7.99 (m, 4 H), 7.56 (d, J=9 Hz, 2 H), 6.98 (d, J=1.6 Hz, 2 H), 6.66 (s, 2 H), 4.2 (s, 4 H), 2.28 (s, 2 H). $^{13}$C NMR (DMSO-$d_6$, 100 MHz): 159.07, 157.02, 146.44, 142.92, 135.31, 124.50, 123.56, 119.81, 109.56, 66.37, 42.41. ESI-MS calculated for $C_{33}H_{16}Na_8O_{38}S_8$ [(M+Na)]$^+$, m/z 1483.90, found [(M−8Na+8 HxA)+2HxA]$^{2+}$, m/z 1149.085.

G2.3. $^1$H NMR (DMSO-$d_6$, 400 MHz): 7.60 (d, J=9 Hz, 2 H), 7.35 (d, J=2 Hz, 2 H), 7.09-7.06 (m, 4 H), 6.97 (d, J=1.8 Hz, 2 H), 4.55 (s, 4 H). $^{13}$C NMR (DMSO-$d_6$, 100 MHz): 174.62, 158.61, 158.46, 157.47, 156.13, 155.68, 152.14, 136.26, 131.07, 116.34, 113.46, 112.04, 110.35, 101.83, 100.74, 68.65. ESI-MS calculated for $C_{32}H_{14}Na_8O_{38}S_8$ [(M+Na)]$^+$, m/z 1469.87, found [(M−8Na+8 HxA)+2HxA]$^{2+}$, m/z 1142.588.

G2.4. $^1$H NMR (DMSO-$d_6$, 400 MHz): 8.15-8.07 (m, 4 H), 7.64 (d, J=9 Hz, 2 H), 7.04 (d, J=1.8 Hz, 2 H), 6.72 (s, 2 H), 4.15 (s, 4 H), 2.11 (s, 4H). $^{13}$C NMR (DMSO-$d_6$, 100 MHz): 173.0, 159.41, 158.31, 157.01, 153.27, 146.41, 142.92, 135.30, 124.50, 123.59, 119.80, 118.77, 109.42, 100.02, 98.85, 68.81, 25.5. ESI-MS calculated for $C_{34}H_{18}N_8O_{38}S_8$ [(M+Na)]$^+$, m/z 1497.95, found [(M−8Na+8 HxA)+2HxA]$^{2+}$, m/z 1156.367.

G2.5. $^1$H NMR (DMSO-$d_6$, 400 MHz): 8.14-8.05 (m, 4 H), 7.63 (d, J=9 Hz, 2 H), 7.03 (d, J=1.8 Hz, 2 H), 6.72 (s, 2 H), 4.1 (s, 4 H), 1.94 (s, 4H), 1.74 (s, 2H). $^{13}$C NMR (DMSO-$d_6$, 100 MHz): 173.6, 159.21, 158.21, 157.01, 153.17, 146.21, 142.52, 135.30, 124.4, 123.95, 119.79, 118.76, 109.45, 100.32, 98.65, 67.81, 25.5, 23.8. ESI-MS calculated for $C_{35}H_{20}Na_8O_{38}S_8$ [(M+Na)]$^+$, m/z 1511.95, found [(M−8Na+8 HxA)+2HxA]$^{2+}$, m/z 1163.163.

G2.6. $^1$H NMR (DMSO-$d_6$, 400 MHz): 8.07 (d, J=2.2 Hz, 2 H), 8.0 (d, J=6.7 Hz, 2 H), 6.98 (d, J=1.9 Hz, 2 H), 6.63 (d, J=1.9 Hz, 2 H), 6.39 (s, 2H), 4.64 (s, 4 H). $^{13}$C NMR (DMSO-$d_6$, 100 MHz): 173.24, 158.43, 158.25, 157.08, 154.28, 148.43, 143.82, 134.31, 123.50, 123.28, 119.84, 118.78, 108.45, 100.05, 98.87, 75.81. ESI-MS calculated for $C_{34}H_{16}Na_8O_{38}S_8$ [(M+Na)]$^+$, m/z 1495.91, found [(M−8Na+8 HxA)+2HxA]$^{2+}$, m/z 1155.620.

EXAMPLE 6

Synthesis of Protected 3', 3'-O-Flavonoid Dimers 10 & 11

Figure 11:
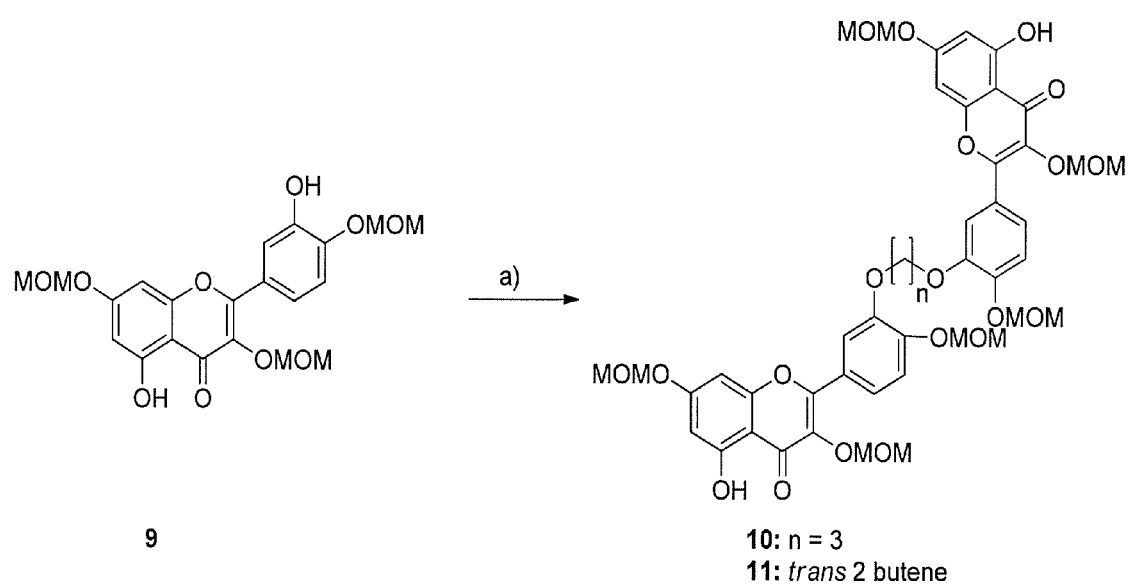
FIG. 11. Synthesis of protected 3',3'-O-flavonoid dimers 10 & 11: a) $K_2CO_3$, dibromoalkane (0.5 equiv), DMF, rt/3 h, 85-90%.

General Procedure for Synthesis of Protected 3',3'-O-Flavonoid Dimers (FIG. 11): To a solution of 9 (1.0 equiv) in N, N-dimethylformamide was added $K_2CO_3$ (2.5 equiv) and stirred for two minutes. This was followed by addition of dibromoalkane (0.5 equiv) and stirred vigorously for 12 hours. After the reaction completed as indicated from TLC the reaction mixture was diluted with EtOAC (25 mL) and water (25 mL). The organic layer was separated and the aqueous phase was extracted with EtOAc (2×25 mL), organic layer was washed with saturated NaCl solution (25 mL). The combined organic layers were dried over anhydrous $Na_2SO_4$, evaporated under reduced pressure to afford crude compounds 10, 11 which were further purified using flash chromatography on silica gel (70-85% ethyl acetate in hexanes).

EXAMPLE 7

Synthesis of Polyphenolic 3', 3'-O-Flavonoid Dimers 10a and 11a

Figure 12:
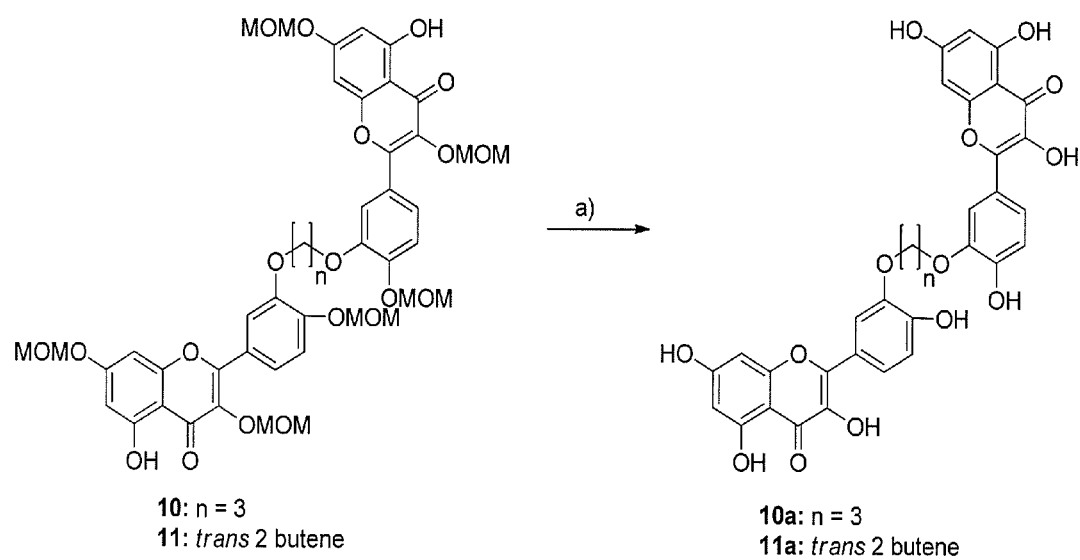
FIG. 12. Synthesis of polyphenolic 3',3'-O-flavonoid dimers: a) p-toluenesulfonic acid, MeOH, reflux/48 h, 55-65%.

General Procedure for Synthesis of Polyphenolic 3',3'-O-Flavonoid Dimers (FIG. 12): The methoxy methyl groups present in the compounds 10, 11 were completely deprotected using following procedure. To a solution of methoxy methylated compound in methanol was taken in a flask attached to a reflux condenser and p-toluenesulfonic acid (catalytic) was added to it. The reaction mixture was stirred at reflux temperature, the extent of deprotection was monitored using UPLC-MS and continued until complete deprotection of all OMOM groups. After completion of the reaction EtOAC (25 mL) was added to precipitate the mixture. The precipitate was filtered, washed with excess EtOAC to remove p-Toluenesulfonic acid and dried to obtain pure polyphenolic compounds 10a, 11a.

EXAMPLE 8

Synthesis of Sulfated 3', 3'-O Flavonoid Dimers G3.1, G3.2

Figure 13:
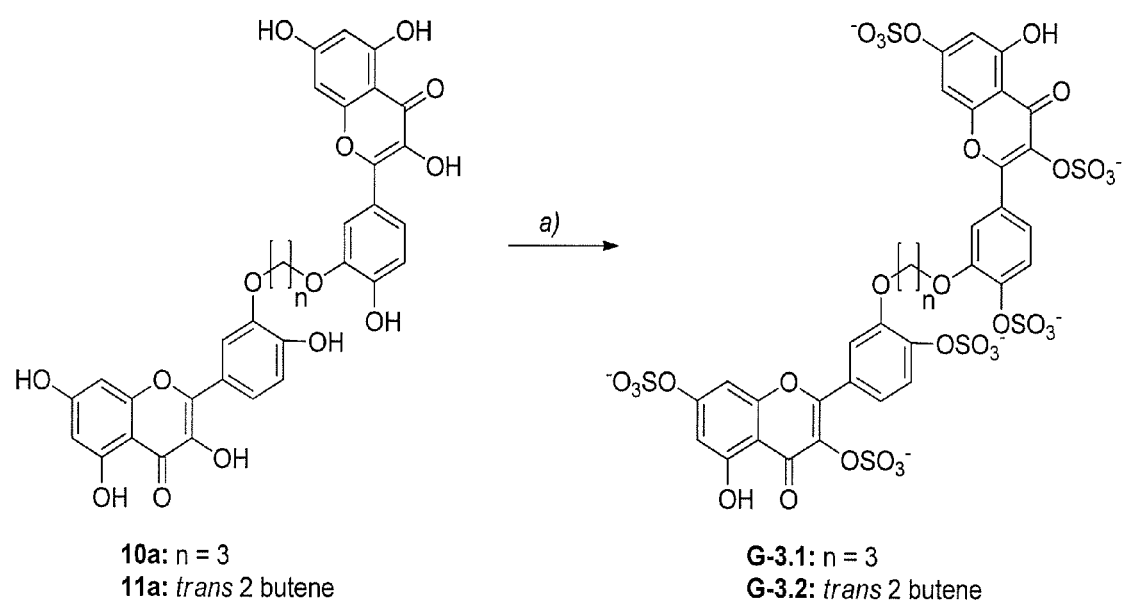
FIG. 13. Synthesis of sulfated 3',3'-O-flavonoid dimers G3.1-G3.2: a) $SO_3$:$Me_3N$, $Et_3N$, $CH_3CN$, microwave/6 h, 75-85%.

General Procedure for Synthesis of Sulfated 3', 3'-O-Flavonoid Dimers (FIG. 13): Sulfation of phenolic precursors 10a, 11a was achieved using microwave-assisted chemical sulfation as described earlier (26,27). Briefly, to a stirred solution of polyphenol in anhydrous $CH_3CN$ (1-5 mL) at room temperature, $Et_3N$ (10 equiv per —OH group) and $Me_3N/SO_3$ complex (6 equiv per —OH) were added. The reaction vessel was sealed and microwaved (CEM Discover, Cary, N.C.) for 6 to 8 h at 90° C. The reaction mixture was cooled and transferred to a roundbottom flask, and the volume was reduced as much as possible under low pressure conditions at 25° C. The reaction mixture was then directly loaded on to a flash chromatography column and purified using a dichloromethane and methanol solvent system (5-30%) to obtain the sulfated flavonoid dimers and trimers. The samples were concentrated and reloaded onto a SP Sephadex C-25 column for sodium exchange. Appropriate fractions were pooled, concentrated in vacuo, and lyophilized to obtain a white powder. Spectral characteristics of all the sulfated compounds G3.1, G3.2 are listed below.

G3.1. $^1$H NMR (DMSO-$d_6$, 400 MHz): 12.33 (s, 2 H), 8.01 (s, 2 H), 7.64-7.56 (m, 4 H), 6.95 (d, J=1.9 Hz, 2 H), 6.58 (d, J=2.0 Hz, 2 H), 4.17 (t, J=2.0 Hz, 4 H), 2.13-2.11 (m, 2 H). $^{13}$C NMR (DMSO-$d_6$, 100 MHz): 177.97, 160.11, 159.60, 155.32, 148.52, 145.74, 133.29, 124.47, 121.16, 119.64, 115.11, 106.08, 101.93, 97.75, 65.50, 52.77. ESI-MS calculated for $C_{33}H_{18}Na_6O_{32}S_6$ $[(M+Na)]^+$, m/z 1279.81, found $[(M-6Na+6\ HxA)+HxA]^+$, m/z 1833.882.

G3.2. $^1$H NMR (DMSO-$d_6$, 400 MHz): 12.34 (s, 2H), 8.03 (d, 2 Hz, 2H), 7.64-7.58 (m, 4 H), 6.92 (d, J=1.8 Hz, 2 H), 6.57 (d, J=1.8 Hz, 2 H), 6.10 (s, 2H), 4.61 (s, 4 H). $^{13}$C NMR (DMSO-$d_6$, 100 MHz): 177.97, 160.14, 159.60, 156.40, 155.30, 148.29, 145.65, 133.35, 128.69, 124.35, 119.46, 114.92, 106.10, 101.96, 97.75, 68.41, 52.78. ESI-MS calculated for $C_{34}H_{18}Na_6O_{32}S_6$ $[(M+Na)]^+$, m/z 1291.82, found $[(M-6Na+6\ HxA)+HxA]^+$, m/z 1845.498.

EXAMPLE 9

Figure 14:
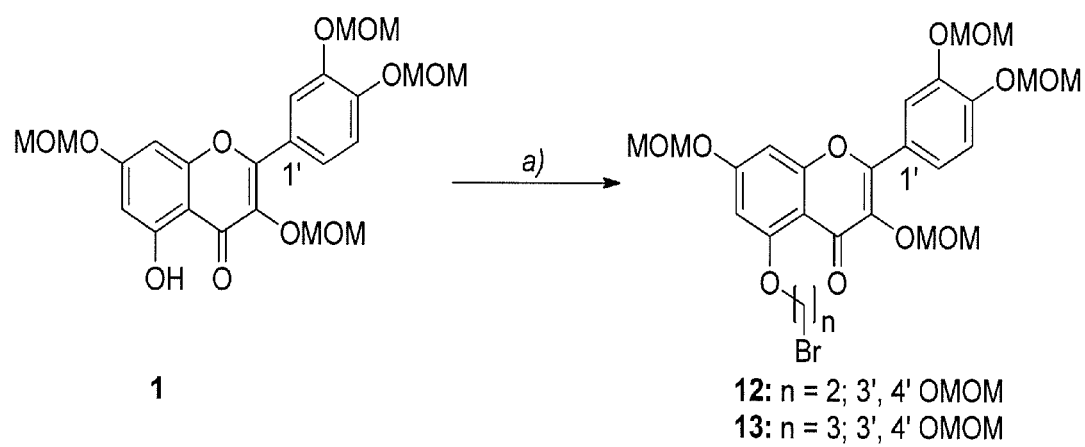
FIG. 14. Synthesis of Intermediate compounds 12 and 13: a) $K_2CO_3$, dibromoalkane (1 equiv), DMF, rt/3 h, 85-90%.

Synthesis of Intermediate Compounds 12 and 13 (FIG. 14)

To a solution of 1 (1.0 equiv) in N, N-dimethylformamide was added $K_2CO_3$ (2.5 equiv) and stirred for two minutes. This was followed by addition of dibromoalkane (1.5. equiv) and stirred vigorously for 12 hours. After the reaction completed as indicated from TLC the reaction mixture was diluted with EtOAC (25 mL) and water (25 mL). The organic layer was separated and the aqueous phase was extracted with EtOAc (2×25 mL), organic layer was washed with saturated NaCl solution (25 mL). The combined organic layers were dried over anhydrous $Na_2SO_4$, evaporated under reduced pressure to afford crude compounds 12 and 13 which were further purified using flash chromatography on silica gel (70-85% ethyl acetate in hexanes).

EXAMPLE 10

Synthesis of Protected 3', 5-O-Flavonoid Trimers 14 and 15

Figure 15:
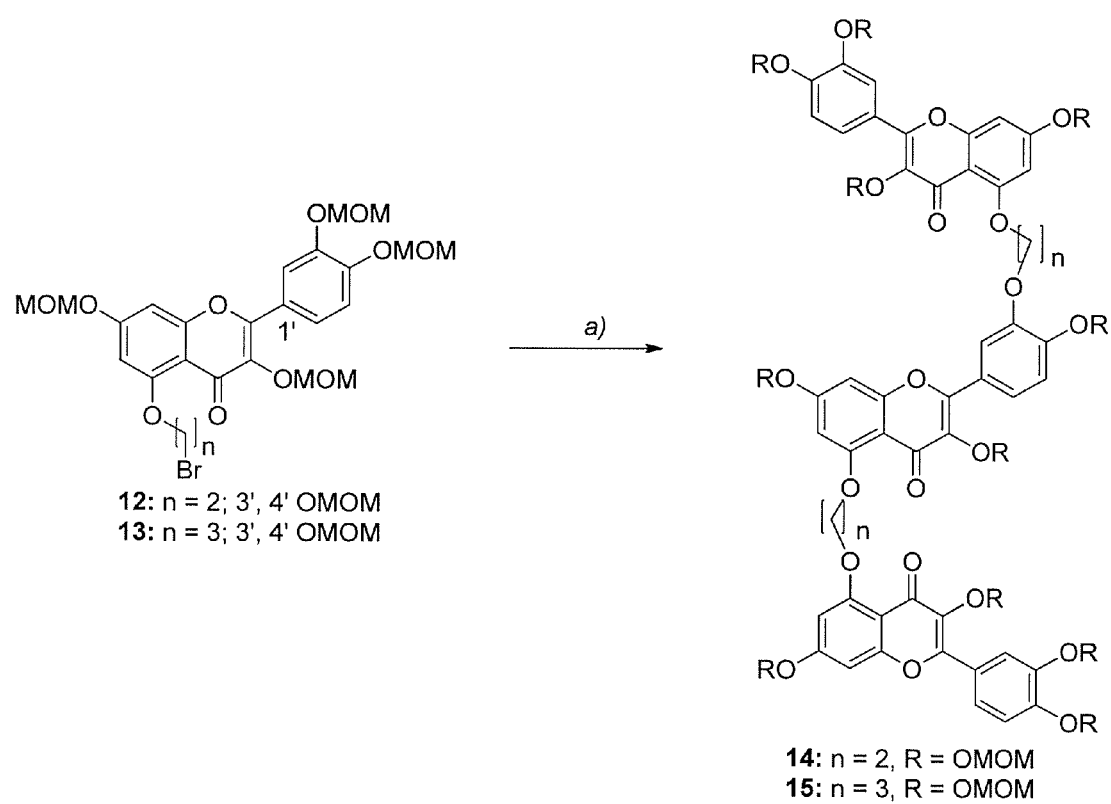
FIG. 15. Synthesis of protected 3',5-O-flavonoid trimers 14 and 15: a) 9, $K_2CO_3$, DMF, 60° C./4 h, 85-90%.

General Procedure for Synthesis of Protected 3', 5-O-Flavonoid Trimers (FIG. 15): To a solution of 12 and 13 (2.0 equiv) and 9 (1.0 equiv) in N, N-dimethylformamide was added $K_2CO_3$ (2.5 equiv) and stirred for two minutes. The reaction mixture was heated at 50° C. for 12 houras. After the reaction completed as indicated from TLC the reaction mixture was diluted with EtOAC (25 mL) and water (25 mL). The organic layer was separated and the aqueous phase was extracted with EtOAc (2×25 mL), organic layer was washed with saturated NaCl solution (25 mL). The combined organic layers were dried over anhydrous $Na_2SO_4$, evaporated under reduced pressure to afford crude compounds 14 and 15 which were further purified using flash chromatography on silica gel (70-85% ethyl acetate in hexanes).

EXAMPLE 11

Synthesis of Polyphenolic 3',5-O-Flavonoid Trimers 14a and 15

Figure 16:
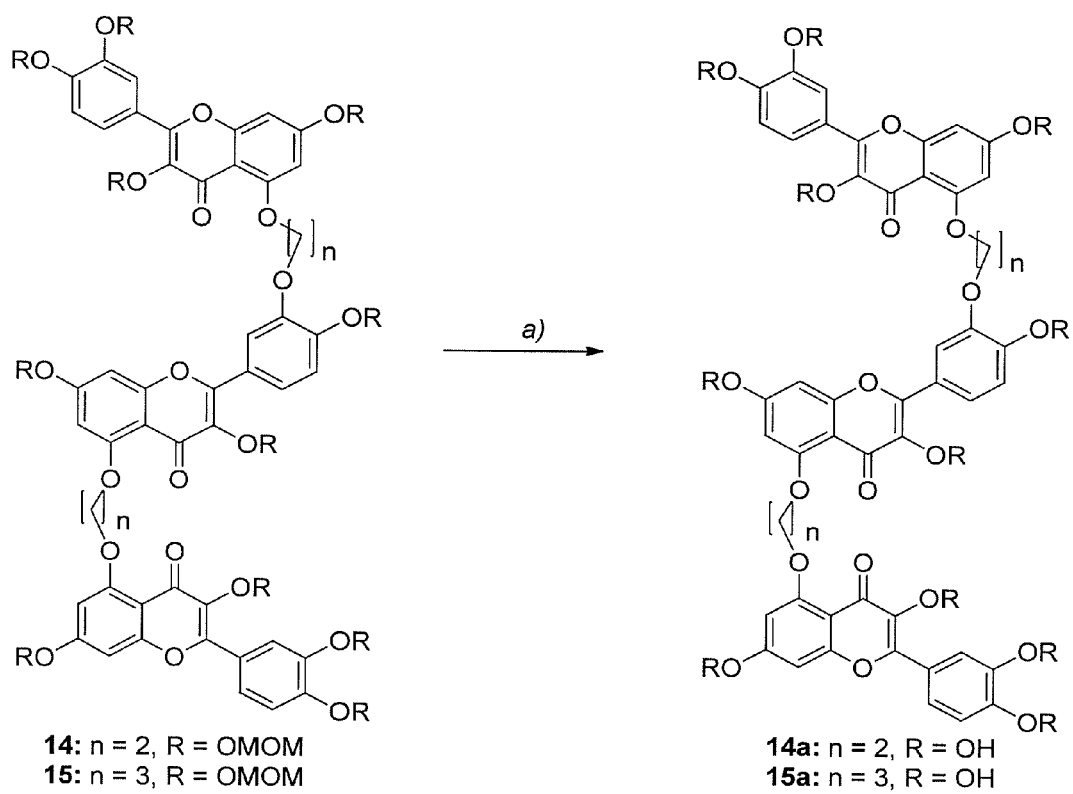
FIG. 16. Synthesis of polyphenolic 3', 5-O-flavonoid trimers 14a and 15a a) p-toluenesulfonic acid, MeOH, reflux/48 h, 55-65%.

General Procedure for Synthesis of Polyphenoiic 3',5-O-Flavonoid Trimers (FIG. 16): The methoxy methyl groups present in the compounds 14 and 15 were completely deprotected using following procedure. To a solution of methoxy methylated compound in methanol was taken in a flask attached to a reflux condenser and p-toluenesulfonic acid (catalytic) was added to it. The reaction mixture was stirred at reflux temperature, the extent of deprotection was monitored using UPLC-MS and continued until complete deprotection of all MOM groups. After completion of the reaction EtOAC (25 mL) was added to precipitate the mixture. The precipitate was filtered, washed with excess EtOAC to remove p-toluenesulfonic acid and dried to obtain pure polyphenolic compounds 14a and 15a.

EXAMPLE 12

Synthesis of Sulfated 3',5-O-Flavonoid Trimers G4.1 and G4.2

Figure 17:
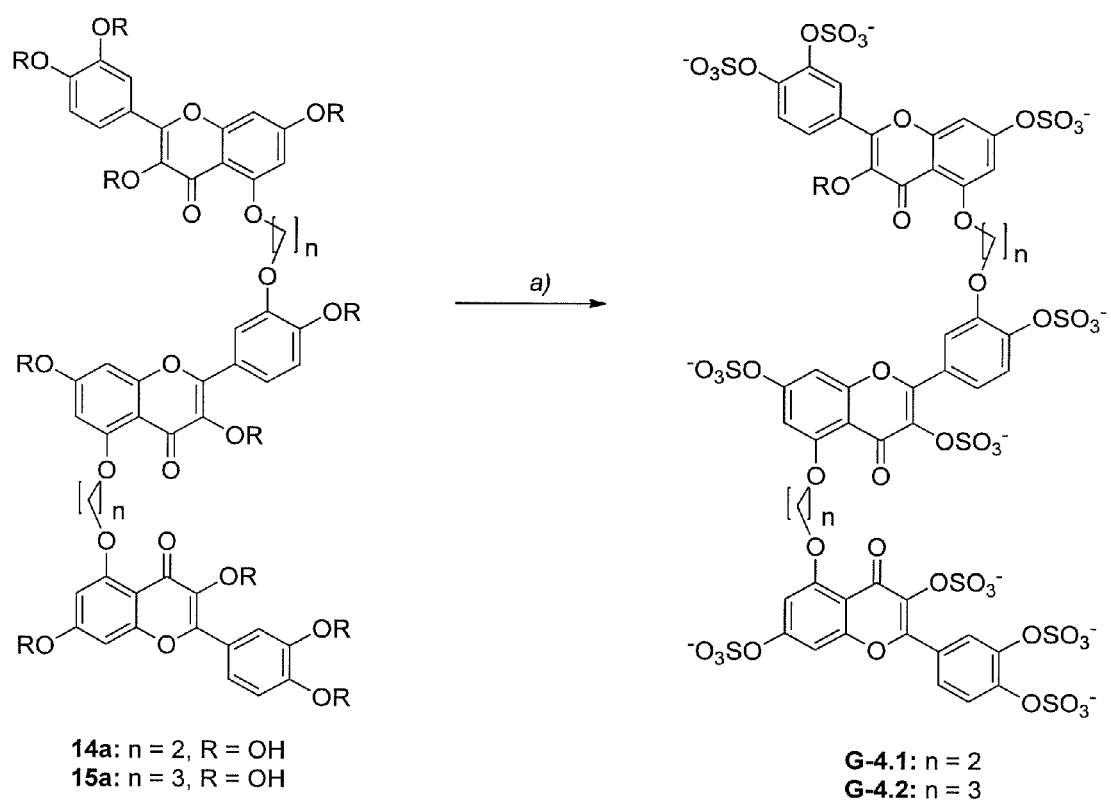
FIG. 17. Synthesis of sulfated 3',5-O-flavonoid trimers G4.1-G4.2: a) $SO_3$:$Me_3N$, $Et_3N$, $CH_3CN$, microwave/8 h, 75-85%.

General Procedure for Synthesis of Sulfated 3',5-O-Flavonoid Trimers (FIG. 17): Sulfation of phenolic precursors 14a or 15a ware achieved using microwave-assisted chemical sulfation as described earlier[1,2]. Briefly, to a stirred solution of polyphenol in anhydrous $CH_3CN$ (1-5 mL) at room temperature, $Et_3N$ (10 equiv per —OH group) and $Me_3N/SO_3$ complex (6 equiv per —OH) were added. The reaction vessel was sealed and microwaved (CEM Discover, Cary, N.C.) for 6 to 8 h at 90° C. The reaction mixture was cooled and transferred to a roundbottom flask, and the volume was reduced as much as possible under low pressure conditions at 25° C. The reaction mixture was then directly loaded on to a flash chromatography column and purified using a dichloromethane and methanol solvent system (5-30%) to obtain the sulfated flavonoid dimers and trimers. The samples were concentrated and reloaded onto a SP Sephadex C-25 column for sodium exchange. Appropriate fractions were pooled, concentrated in vacuo, and lyophilized to obtain a white powder. Spectral characteristics of all the sulfated compounds G4.1 and G4.2 are listed below.

G4.1. $^1$H NMR (DMSO-$d_6$, 400 MHz): 8.18-8.06 (m, 5 H), 7.79-7.63 (m, 4 H), 7.31-7.14 (m, 3 H), 6.92-6.74 (m, 3 H), 4.52 (s, 6 H), 4.42 (s, 2 H). $^{13}$C NMR (DMSO-$d_6$, 100 MHz): 170.92, 170.81, 162.38, 162.34, 159.47, 157.94, 157.89, 148.61, 146.95, 146.26, 145.04, 141.98, 141.92, 141.63, 137.24, 137.12, 137.09, 127.99, 125.47, 122.42, 122.26, 121.49, 119.11, 115.84, 115.58, 114.51, 113.50, 105.52, 105.44, 97.71, 95.20, 95.10, 67.84, 67.72, 59.69. ESI-MS calculated for $C_{49}H_{23}Na_{11}O_{54}S_{11}$ $[(M+Na)]^+$, m/z 2104.28, found $[(M-11Na+11\ HxA)+2HxA]^{2+}$, m/z 1578.349.

G4.2. $^1$H NMR (DMSO-$d_6$, 400 MHz): 8.14-8.06 (m, 5 H), 7.68-7.62 (m, 4 H), 7.16-7.05 (m, 3 H), 6.79-6.63 (m, 3 H), 4.32 (s, 6 H), 4.24 (s, 2 H), 2.35-2.27 (m, 4 H). $^{13}$C NMR (DMSO-$d_6$, 100 MHz): 171.92, 170.29, 162.48, 162.64, 159.67, 157.85, 157.19, 149.81, 145.85, 146.86, 144.04, 140.68, 141.82, 140.73, 137.64, 137.32, 137.19, 127.88, 124.48, 123.41, 122.26, 121.49, 119.11, 115.84, 115.58, 114.51, 113.50, 105.52, 105.44, 97.71, 95.20, 95.10, 66.94, 66.68. ESI-MS calculated for $C_{49}H_{23}Na_{11}O_{54}S_{11}$ [(M+Na)]$^+$, m/z 2132.33, found [(M−11Na+11 HxA)+2HxA]$^{2+}$, m/z 1592.727.

EXAMPLE 13

Study of Flavanoid Oligomers in Mice Tumor Xenograft Model

Figure 18A:
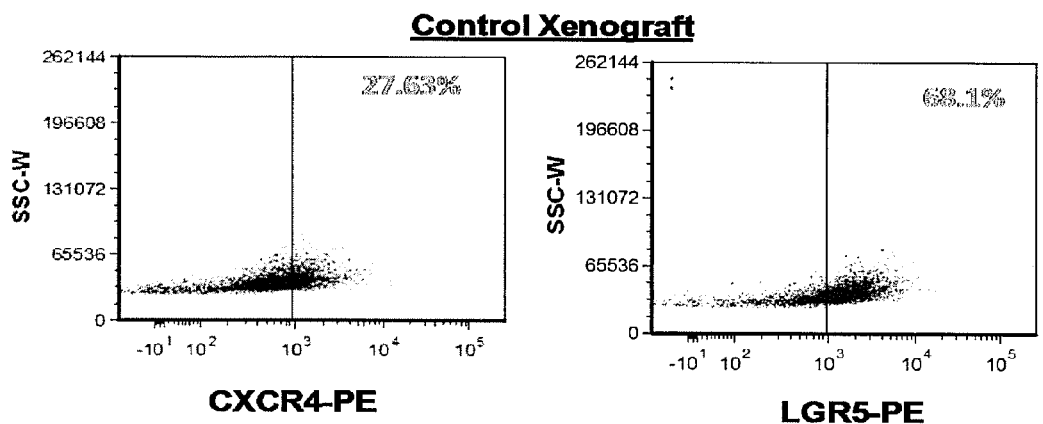
FIG. 18A-B. Study of Flavanoid Oligomers in Mice Tumor Xenograft Model. Cell suspensions from the (A) control and (B) G2.2 mice tumor samples were incubated with PE conjugated LGR5 or CXCR4 antibody for 30 minutes, washed two times with PBS buffer, and then analyzed.
Figure 18B:
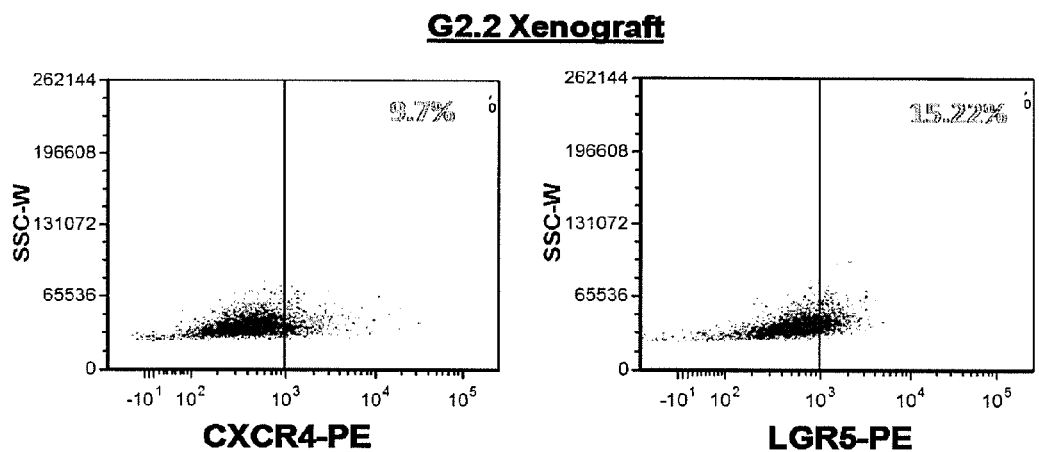

One million HCT116 cells were washed with PBS and injected subcutaneously (0.2 mL cell suspension in 50% matrigel) into 6-week-old NOD-SCID mice (Taconic Incorporation, Germantown, N.Y.) on both flanks. Once the tumors become palpable, 16 mice were randomized into two groups. In the treatment group, animals received direct intratumoral (IT) injection of appx 1.125 mg of G2.2 dissolved in 75 µl PBS (pH=7.4) solution three times a week for three weeks (a total of 10 mg of G2.2 over three weeks). Control animals were also received IT injection with 75 µl of vehicle alone (PBS) on the same schedule. Tumor size was measured three times a week using caliber and tumor volume was calculated as previously described. Mice were also weighed three times a week. All the animals were sacrificed within 1 week after completion of therapy using approved method of $CO_2$ asphyxiation. Tumor xenografts were minced with scalpels blade into small pieces and then digested in DMEM/F12 medium containing 300 units/mL collagenase (Stem Cell Technologies) and 100 units/mL hyaluronidase (Stem Cell Technologies) for 1 hr at 37° C. Cells were then washed and re-suspended to a final concentration of $10^6$ cell/mL in DMEM/2% FBS. Cell suspensions from the tumor samples were incubated with PE conjugated LGR5 or CXCR4 antibody for 30 minutes and washed two times with PBS buffer and then analyzed (FIG. 18A-B). Results indicate that 1) intratumoral treatment with G2.2 had no effect on overall animal weight; 2) Intratumoral treatment with G2.2 caused a modest 20-42% reduction in tumor volume between days 5-19 (not shown). However, none of these values were statistically significant (p>0.1). In fact, these findings are in line with our in vitro data suggesting minimal effect of G2.2 on bulk tumor cells. 3) Despite the modest reduction tumor volume, G2.2 treated xenografts demonstrated a robust attenuation of LGR5 (~78%) as well as CXCR4 (~75%) positive cells compared to vehicle treated xenografts (FIG. 18A-B). These results strongly support the contention that G2.2 selectively inhibits CSCs growth/self-renewal both in vitro and in vivo.

REFERENCES

1. Gangemi, R., Paleari, L., Orengo, A. M., Cesario, A., Chessa, L., Ferrini, S., and Russo, P. (2009) Cancer stem cells: a new paradigm for understanding tumor growth and progression and drug resistance. *Curr. Med. Chem.* 16, 1688-1703.
2. Dontu, G., Abdallah, W. M., Foley, J. M., Jackson, K. W., Clarke, M. F., Kawamura, M. J., and Wicha, M. S. (2003) In vitro propagation and transcriptional profiling of human mammary stem/progenitor cells. *Genes Dev.* 17, 1253-1270.
3. Reya, T., Morrison, S. J., Clarke, M. F., and Weissman, I. L. (2001) Stem cells, cancer, and cancer stem cells. *Nature* 414, 105-111.
4. Scatena, R., Bottoni, P., Pontoglio, A., and Giardina, B. (2011) Cancer stem cells: the development of new cancer therapeutics. *Expert Opin. Biol. Ther.* 11, 875-892.
5. Gupta, P. B., Onder, T. T., Jiang, G., Tao, K., Kuperwasser, C., Weinberg, R. A., and Lander, E. S. (2009) Identification of selective inhibitors of cancer stem cells by high-throughput screening. *Cell* 138, 645-659.
6. Carmody, L., Germain, A., Morgan, B., VerPlank, L., Fernandez, C., Feng, Y., Perez, J., Dandapani, S., Munoz, B., Palmer, M., Lander, E. S., Gupta, P. B., and Schreiber, S. L. Probe Reports from the NIH Molecular Libraries Program [Internet]. Bethesda (Md.): National Center for Biotechnology Information (US). (2010-2011) PMID: 23762939.
7. Carmody, L. C., Germain, A. R., VerPlank, L., Nag, P. P., Munoz, B., Perez, J. R., and Palmer, M. A. (2012) Phenotypic high-throughput screening elucidates target pathway in breast cancer stem cell-like cells. *J. Biomol. Screen.* 17, 1204-1210.
8. Germain, A. R., Carmody, L. C., Nag, P. P., Morgan, B., Verplank, L., Fernandez, C., Donckele, E., Feng, Y., Perez, J. R., Dandapani, S., Palmer, M., Lander, E. S., Gupta, P. B., Schreiber, S. L., and Munoz, B. (2013) Cinnamides as selective small-molecule inhibitors of a cellular model of breast cancer stem cells. *Bioorg. Med. Chem. Lett.* 23, 1834-1838.
9. Ailles, L. E., and Weissman, I. L. (2007) Cancer stem cells in solid tumors. *Curr. Opin. Biotechnol.* 18, 460-466.
10. Reya, T., and Clevers, H. (2005) Wnt signaling in stem cells and cancer. *Nature* 434, 843-850
11. Kraushaar, D. C., Dalton, S., and Wang, L. (2013) Heparan sulfate: a key regulator of embryonic stem cell fate. *Biol. Chem.* 394, 741-751.
12. Hirano, K., Sasaki, N., Ichimiya, T., Miura, T., Van Kuppevelt, T. H., and Nishihara, S. (2012) 3-O-sulfated heparan sulfate recognized by the antibody HS4C3 contribute to the differentiation of mouse embryonic stem cells via Fas signaling. *PLoS One* 7, e43440.
13. Johnson, C. E., Crawford, B. E., Stavridis, M., Ten Dam, G., Wat, A. L., Rushton, G., Ward, C M., Wilson, V., van Kuppevelt, T. H., Esko, J. D., Smith, A., Gallagher, J. T., and Merry, C. L. (2007) Essential alterations of heparan sulfate during the differentiation of embryonic stem cells to Sox1-enhanced green fluorescent protein-expressing neural progenitor cells. *Stem Cells* 25, 1913-1923.
14. Nairn, A. V., Kinoshita-Toyoda, A., Toyoda, H., Xie, J., Harris, K., Dalton, S., Kulik, M., Pierce, J. M., Toida, T., Moremen, K. W., and Linhardt, R. J. (2007) Glycomics of proteoglycan biosynthesis in murine embryonic stem cell differentiation. *J. Proteome Res.* 6, 4374-4387.
15. Campoli, M., Ferrone, S., and Wang, X. (2010) Functional and clinical relevance of chondroitin sulfate proteoglycan 4. *Adv. Cancer Res.* 109, 73-121.
16. Lombardo, Y., Scopelliti, A., Cammareri, P., Todaro, M., Iovino, F., Ricci-Vitiani, L., Gulotta, G., Dieli, F., de Maria, R., Stassi, G. (2011) Bone morphogenetic protein 4 induces differentiation of colorectal cancer stem cells and increases their response to chemotherapy in mice. *Gastroenterology* 140, 297-309.
17. Battula, V. L., Shi, Y., Evans, K. W., Wang, R. Y., Spaeth, E. L., Jacamo, R. O., Guerra, R., Sahin, A. A., Marini, F. C., Hortobagyi, G., Mani, S. A., and Andreeff, M. (2012) Ganglioside GD2 identifies breast cancer stem cells and promotes tumorigenesis. *J. Clin. Invest.* 122, 2066-2078.

18. Desai, U. R. (2013) The promise of sulfated synthetic small molecules as modulators of glycosaminoglycan function. *Future Med. Chem.* 5, 1363-1366.
19. Raman, K., Karuturi, R., Swarup, V. P., Desai, U. R., and Kuberan, B. (2012) Discovery of novel sulfonated small molecules that inhibit vascular tube formation. *Bioorg. Med. Chem. Lett.* 22, 4467-4470.
20. Al-Horani, R. A., Ponnusamy, P., Mehta, A. Y., Gailani, D., and Desai, U. R. (2013) Sulfated pentagalloylglucoside is a potent, allosteric, and selective inhibitor of factor XIa. *J. Med. Chem.* 56, 867-878.
21. Karuturi, R., Al-Horani, R. A., Mehta, S. C., Gailani, D., and Desai, U. R. (2013) Discovery of allosteric modulators of factor XIa by targeting hydrophobic domains adjacent to its heparin-binding site. *J. Med. Chem.* 56, 2415-2428.
22. Sidhu, P. S., Abdel Aziz, M. H., Sarkar, A., Mehta, A. Y., Zhou, Q., and Desai, U. R. (2013) Designing allosteric regulators of thrombin. Exosite 2 features multiple subsites that can be targeted by sulfated small molecules for inducing inhibition. *J. Med. Chem.* 56, 5059-5070.
23. Gunnarsson, G. T., and Desai, U. R. (2002) Designing small, nonsugar activators of antithrombin using hydropathic interaction analyses. *J. Med. Chem.* 45, 1233-1243.
24. Gunnarsson, G. T., and Desai, U. R. (2002) Interaction of designed sulfated flavanoids with antithrombin: lessons on the design of organic activators. *J. Med. Chem.* 45, 4460-4470.
25. Al-Horani, R. A., Liang, A., and Desai, U. R. (2011) Designing nonsaccharide, allosteric activators of antithrombin for accelerated inhibition of factor Xa. *J. Med. Chem.* 54, 6125-6138.
26. Al-Horani, R. A., and Desai, U. R. (2010) Chemical sulfation of small molecules—advances and challenges. *Tetrahedron* 66, 2907-2918.
27. Kanwar, S. S., Yu, Y., Nautiyal, J., Patel, B. B., and Majumdar, A. P. (2010) The Wnt/beta-catenin pathway regulates growth and maintenance of colonospheres. *Mol. Cancer* 9, 212.
28. Vaiopoulos, A. G., Kostakis, I. D., Koutsilieris, M., and Papavassiliou, A. G. (2012) Colorectal cancer stem cells. *Stem Cells* 30, 363-371.
29. Hermann, P. C., Huber, S L., Herrler, T., Aicher, A., Ellwart, J. W., Guba, M., Bruns, C. J., and Heeschen, C. (2007) Distinct populations of cancer stem cells determine tumor growth and metastatic activity in human pancreatic cancer. *Cell Stem Cell* 1, 313-323.
30. Barker, N., Ridgway, R. A., van Es, J. H., van de Wetering, M., Begthel, H., van den Born, M., Danenberg, E., Clarke, A. R., Sansom, O. J., and Clevers, H. (2009) Crypt stem cells as the cells-of-origin of intestinal cancer. *Nature* 457, 608-611.
31. Sanchez-Ripoll, Y., Bone, H, K., Owen, T., Guedes, A. M., Abranches, E., Kumpfmueller, B., Spriggs, R. V., Henrique, D., and Welham, M. J. (2013) Glycogen synthase kinase-3 inhibition enhances translation of pluripotency-associated transcription factors to contribute to maintenance of mouse embryonic stem cell self-renewal. *PLoS One* 8, e60148.
32. Gonsalves, F. C., Klein, K., Carson, B. B., Katz, S., Ekas, L. A., Evans, S., Nagourney, R., Cardozo, T., Brown, A. M., and DasGupta, R. (2011) An RNAi-based chemical genetic screen identifies three small-molecule inhibitors of the Wnt/wingless signaling pathway. *Proc. Natl. Acad. Sci. USA* 108, 5954-5963.
33. Nakanishi, Y., Seno, H., Fukuoka, A., Ueo, T., Yamada, Y., Maruno, T., Nakanishi, N., Kanda, K., Komekado, H., Kawada, M., Isomura, A., Kawada, K., Sakai, Y., Yanagita, M., Kageyama, R., Kawaguchi, Y., Taketo, M. M., Yonehara, S., and Chiba, T. (2013) Dclk1 distinguishes between tumor and normal stem cells in the intestine. *Nat. Genet.* 45, 98-103.
34. Prasetyanti, P. R., Zimberlin, C. D., Bots, M., Vermeulen, L., Melo Fde, S., and Medema, J. P. (2013) Regulation of stem cell self-renewal and differentiation by Wnt and Notch are conserved throughout the adenoma-carcinoma sequence in the colon. *Mol. Cancer* 12, 126.
35. Kreso, A., van Galen, P., Pedley, N. M., Lima-Fernandes, E., Frelin, C., Davis, T., Cao, L., Baiazitov, R., Du, W., Sydorenko, N., Moon, Y. C., Gibson, L., Wang, Y., Leung, C., Iscove, N. N., Arrowsmith, C. H., Szentgyorgyi, E., Gallinger, S., Dick, J. E., and O'Brien, C. A. (2014) Self-renewal as a therapeutic target in human colorectal cancer. *Nat. Med.* 20, 29-36.
36. Ferro, V., Dredge, K., Liu, L., Hammond, E., Bytheway, I., Li, C., Johnstone, K., Karoli, T., Davis, K., Copeman, E., and Gautam, A. (2007) PI-88 and novel heparan sulfate mimetics inhibit angiogenesis. *Semin. Thromb. Hemost.* 33, 557-568.
Lewis, K. D., Robinson, W. A., Millward, M. J., Powell, A., Price, J., Thomson, D. B., Walpole, E. T., Haydon, A. M., Creese, B. R., Roberts, K. L., Zalcberg, J. R., and Gonzalez R. (2008) A phase II study of the heparanase inhibitor PI-88 in patients with advanced melanoma. *Invest. New Drugs* 26, 89-94.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. Sulfated flavonoid dimers having the general formula of formula I:

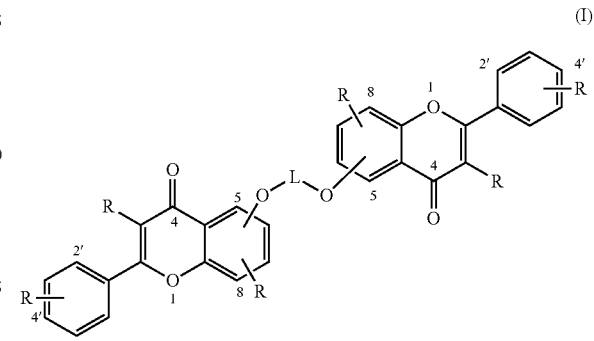

wherein
R is one or more of —OH, or —OSO$_3^-$M$^+$ or —H, each of which may be the same or different, wherein at least one —OSO$_3^-$M$^+$ group is present in the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;
L is any one of linkers L$_1$ through L$_9$ shown below wherein n is 1-10; and

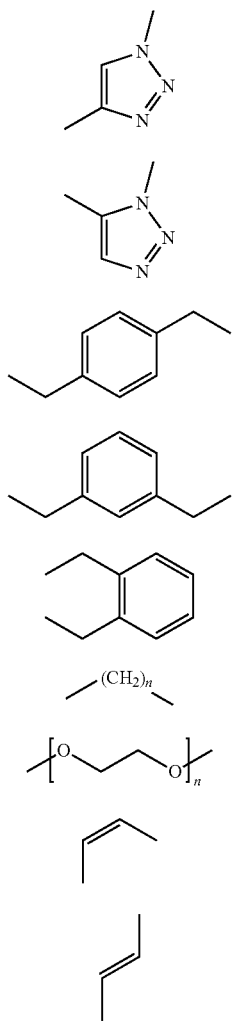

the two flavonoid units are connected through either 5-5, 5-6, 5-7, 5-8, 6-6, 6-7, 6-8, 7-7, 7-8, or 8-8 linkages.

2. Sulfated flavonoid dimers having the general formula of formula II:

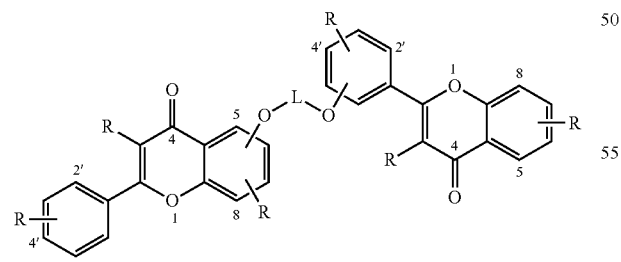

(II)

wherein

R is one or more of —OH, or —$OSO_3^-M^+$ or —H, each of which may be the same or different, wherein at least one —$OSO_3^-M^+$ group is present on the molecule and wherein M is selected from the group consisting of $Na^+$, $K^+$, $Li^+$, $NH_4^+$, $NR'_4^+$, $Mg^{2+}$, $Ca^{2+}$ or other metal cations, wherein R' is H or alkyl or aryl groups;

L is any one of linkers $L_1$ through $L_9$ shown below wherein n is 1-10; and

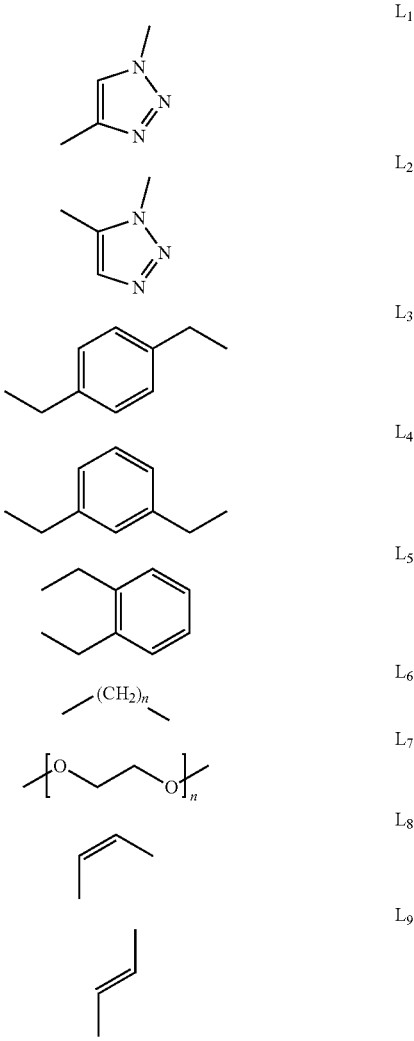

the two flavonoid units are connected through either 5-2', 5-3', 5-4', 6-2', 6-3', 6-4', 7-2', 7-3', 7-4', 8-2', 8-3', or 8-4' linkages.

3. Sulfated flavonoid dimers having the general formula of formula III:

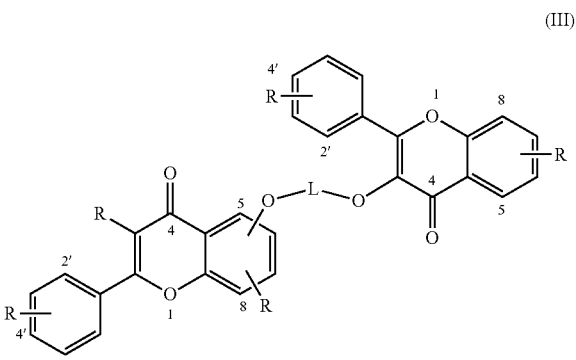

(III)

wherein

R is one or more of —OH, or —OSO$_3^-$M$^+$ or —H, each of which may be the same or different, wherein at least one —OSO$_3^-$M$^+$ group is present on the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

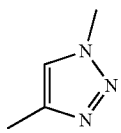
L$_1$

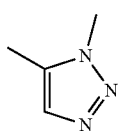
L$_2$

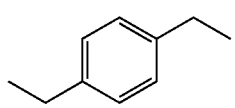
L$_3$

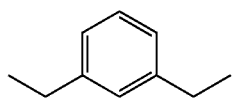
L$_4$

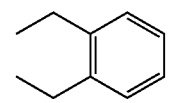
L$_5$

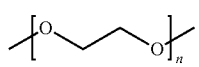
L$_6$

L$_7$

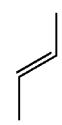
L$_8$

L$_9$ the two flavonoid units are connected through either 5-3, 6-3, 7-3, or 8-3 linkages.

4. Sulfated flavonoid dimers having the general formula of formula IV:

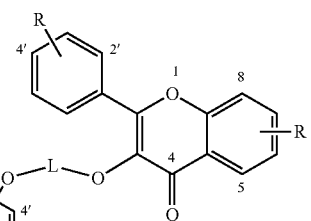
(IV)

wherein

R is one or more of —OH, or —OSO$_3^-$M$^+$ or —H, each of which may be the same or different, wherein at least one —OSO$_3^-$M$^+$ group is present on the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$

L$_2$

L$_3$

L$_4$

L$_5$

L$_6$

L$_7$

L$_8$

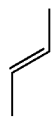

L9 the two flavonoid units are connected through either 2'-3, 3'-3, or 4'-3 linkages.

5. Sulfated flavonoid dimers having the general formula of formula V:

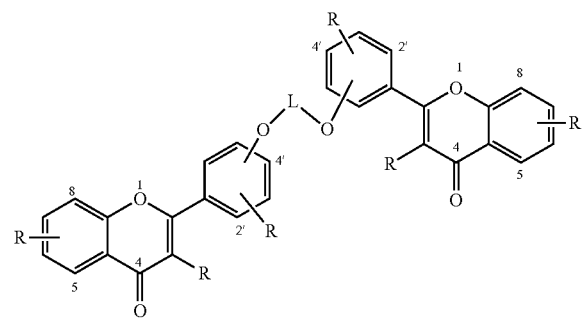

(V)

wherein

R is one or more of —OH, or —OSO$_3^-$M$^+$ or —H, each of which may be the same or different, wherein at least one —OSO$_3^-$M$^+$ group is present on the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$

L$_2$

L$_3$

L$_4$

L$_5$

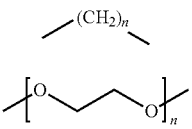

L$_6$

L$_7$

L$_8$

L$_9$ the two flavonoid units are connected through either 2'-2', 2'-3', 2'-4', 3'-3', 3'-4', or 4'-4' linkages.

6. Sulfated flavonoid dimers having the general formula of formula VI:

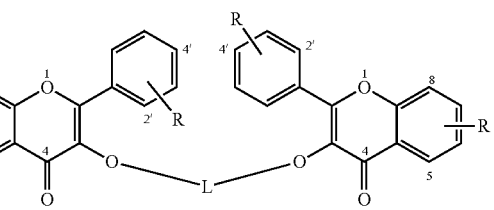

(VI)

wherein

R is one or more of —OH, or —OSO$_3^-$M$^+$ or —H, each of which may be the same or different, wherein at least one —OSO$_3^-$M$^+$ group is present on the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$

L$_2$

L$_3$

L$_4$

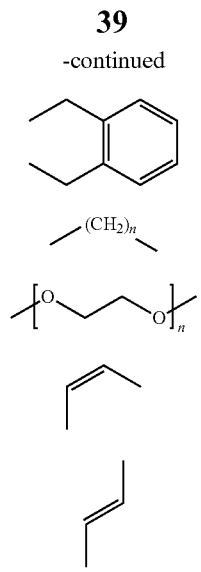 L5

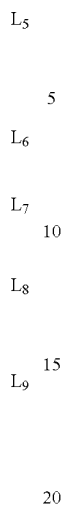 L8

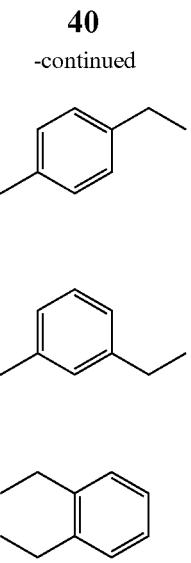 L9 any two flavonoid units are connected through 3-3 linkage.

7. Sulfated flavonoid trimers having the general formula of formula VII:

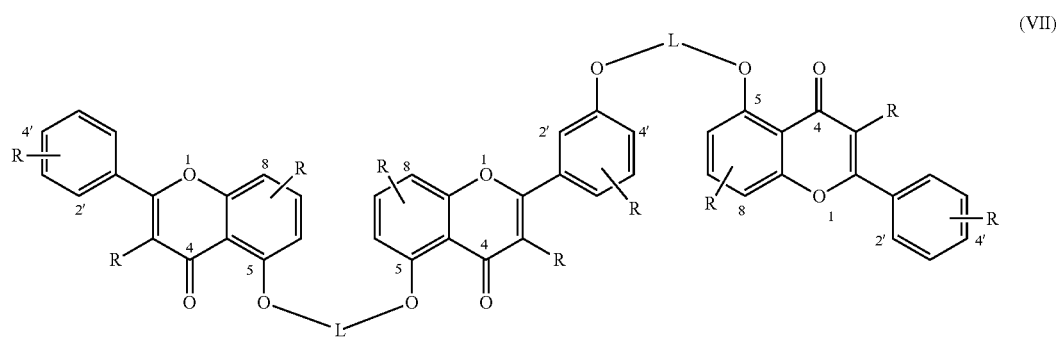

(VII)

wherein

R is one or more of —OH, or —OSO$_3^-$M$^+$ or —H, each of which may be the same or different, wherein at least one —OSO$_3^-$M$^+$ group is present on the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

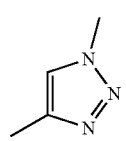 L1

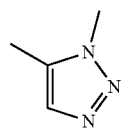 L2

—(CH$_2$)$_n$— L3

L4

L5

—(CH$_2$)$_n$— L6

[O—O]$_n$ L7

L8

L9 any two flavonoid units are connected through either 5-5, 5-6, 5-7, 5-8, 6-6, 6-7, 6-8, 7-7, 7-8, or 8-8 linkages.

8. Sulfated flavonoid tetramers having the general formula of formula VIII:

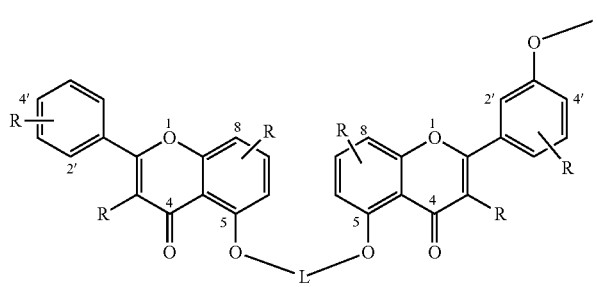

wherein
R is one or more of —OH, or —OSO$_3^-$M$^+$ or —H each of which may be the same or different, wherein at least one —OSO$_3^-$M$^+$ group is present on the molecule and wherein M is selected from the group consisting of Na$^+$, K$^+$, Li$^+$, NH$_4^+$, NR'$_4^+$, Mg$^{2+}$, Ca$^{2+}$ or other metal cations, wherein R' is H or alkyl or aryl groups;

L is any one of linkers L$_1$ through L$_9$ shown below wherein n is 1-10; and

L$_1$
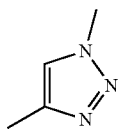

L$_2$
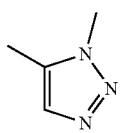

L$_3$
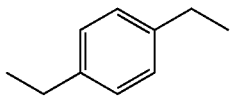

L$_4$
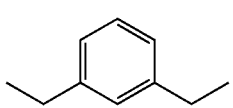

-continued

L$_5$
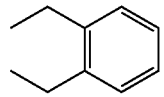

L$_6$
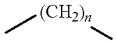

L$_7$
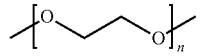

L$_8$

L$_9$ any two flavonoid units are connected through either 5-5, 5-6, 5-7, 5-8, 6-6, 6-7, 6-8, 7-7, 7-8, or 8-8 linkages.

9. Sodium 4-(5-(3-((2-(3,4-bis(sulfonatooxy)phenyl)-4-oxo-3,7-bis(sulfonatooxy)-4H-chromen-5-ypoxy)propoxy)-4-oxo-3,7-bis(sulfonatooxy)-4H-chromen-2-yl)-1,2-phenylene bis(sulfate).

10. Sodium 4-(5-(2-((2-(3,4-bis(sulfonatooxy)phenyl)-4-oxo-3,7-bis(sulfonatooxy)-4H-chromen-5-yl)oxy)ethoxy)-4-oxo-3 ,7-bis(sulfonatooxy)-4H-chromen-2-yl)-1,2-phenylene bis(sulfate).

* * * * *